United States Patent
Harkin et al.

(10) Patent No.: US 10,881,539 B2
(45) Date of Patent: Jan. 5, 2021

(54) IMPLANTABLE BIOCOMPATIBLE EXPANDER SUITABLE FOR TREATMENT OF CONSTRICTIONS OF BODY LUMEN

(71) Applicant: THE PROVOST, FELLOWS, FDN SCHOLARS & THE OTHER MEMBERS OF BOARD, OF THE COLLEGE OF THE HOLY & UNDIV. TRINITY OF QUEEN ELIZABETH, Dublin (IE)

(72) Inventors: Conor Harkin, Dublin (IE); Garrett Ryan, Dublin (IE); Bruce Murphy, Dublin (IE); James Redmond, Dublin (IE)

(73) Assignee: The Provost, Fellows, Foundation Scholars & The Other Members of Board, of The College of The Holy & Undiv. Trinity of Queen Elizabeth, Near Dublin, Dublin (IE)

( * ) Notice: Subject to any disclaimer, the term of this patent is extended or adjusted under 35 U.S.C. 154(b) by 111 days.

(21) Appl. No.: 15/775,257

(22) PCT Filed: Nov. 14, 2016

(86) PCT No.: PCT/EP2016/077606
§ 371 (c)(1),
(2) Date: May 10, 2018

(87) PCT Pub. No.: WO2017/081326
PCT Pub. Date: May 18, 2017

(65) Prior Publication Data
US 2018/0325705 A1 Nov. 15, 2018

Related U.S. Application Data

(60) Provisional application No. 62/321,639, filed on Apr. 12, 2016.

(30) Foreign Application Priority Data

Nov. 12, 2015 (EP) .................................... 15194391

(51) Int. Cl.
*A61F 2/86* (2013.01)
*A61F 2/04* (2013.01)
(Continued)

(52) U.S. Cl.
CPC ................ *A61F 2/86* (2013.01); *A61B 1/307* (2013.01); *A61F 2/04* (2013.01); *A61F 2/848* (2013.01);
(Continued)

(58) Field of Classification Search
CPC ........................................................ A61F 2/04
See application file for complete search history.

(56) References Cited

U.S. PATENT DOCUMENTS

| 4,580,568 A | * | 4/1986 | Gianturco | ............. | A61M 29/02 606/198 |
| 5,035,706 A | | 7/1991 | Giantureo et al. | | |

(Continued)

FOREIGN PATENT DOCUMENTS

| CN | 101945621 A | 1/2011 |
| CN | 202822454 U | 3/2013 |

(Continued)

OTHER PUBLICATIONS

Notification of Transmittal of the International Search Report and the Written Opinion of the International Searching Authority, or the Declaration, PCT/EP2016/077606, entitled: "An Implantable Biocompatible Expander Suitable for Treatment of Constrictions of Body Lumen," dated Jul. 4, 2017.
(Continued)

*Primary Examiner* — Katrina M Stransky
(74) *Attorney, Agent, or Firm* — Hamilton, Brook, Smith & Reynolds, P.C.

(57) ABSTRACT

An implantable biocompatible expander suitable for implantation into a urinary duct, comprises an elongated sinusoidal ring comprising at least two proximal prongs and at least two distal prongs, wherein the expander is resiliently deformable from a relaxed radially expanded orientation to a radially contracted orientation suitable for transluminal delivery through the urinary duct. The expander is configured to exert an outward radial force against a wall of the urinary duct when in-situ within the urinary duct. In particular, the expander is suitable for treatment of benign prostatic hyperplasia and configured for implantation into the prostatic urethra between, and substantially spanning the prostatic urethra between, the bladder neck and external sphincter.

20 Claims, 19 Drawing Sheets

(51) Int. Cl.

| | | |
|---|---|---|
| A61F 2/966 | (2013.01) | |
| A61F 2/848 | (2013.01) | |
| A61M 29/02 | (2006.01) | |
| A61F 2/82 | (2013.01) | |
| A61B 1/307 | (2006.01) | |

(52) U.S. Cl.
CPC ............ *A61F 2/966* (2013.01); *A61M 29/02* (2013.01); *A61F 2002/047* (2013.01); *A61F 2002/825* (2013.01); *A61F 2002/8483* (2013.01); *A61F 2002/9665* (2013.01); *A61F 2210/0004* (2013.01); *A61F 2230/0013* (2013.01); *A61F 2230/0023* (2013.01); *A61F 2230/0054* (2013.01); *A61F 2230/0056* (2013.01); *A61F 2230/0067* (2013.01); *A61F 2230/0069* (2013.01); *A61F 2230/0095* (2013.01); *A61F 2250/0039* (2013.01); *A61F 2250/0067* (2013.01)

(56) References Cited

U.S. PATENT DOCUMENTS

| | | | |
|---|---|---|---|
| 5,159,920 A | 11/1992 | Condon et al. | |
| 5,269,802 A | 12/1993 | Garber | |
| 5,591,277 A | 1/1997 | Braunheim | |
| 5,599,325 A | 2/1997 | Ju et al. | |
| 5,674,278 A | 10/1997 | Boneau | |
| 5,697,967 A | 12/1997 | Dinh et al. | |
| 5,830,179 A | 11/1998 | Mikus et al. | |
| 10,682,245 B2 | 6/2020 | Harkin | |
| 2006/0100688 A1 | 5/2006 | Jordan et al. | |
| 2007/0077266 A1 | 4/2007 | Egashira | |
| 2009/0171442 A1 | 7/2009 | Young et al. | |
| 2009/0210045 A1 | 8/2009 | Sorensen et al. | |
| 2010/0137893 A1 | 6/2010 | Kilemnick et al. | |
| 2010/0152835 A1* | 6/2010 | Orr | A61F 2/07 623/1.15 |
| 2011/0301690 A1* | 12/2011 | Giasolli | A61F 2/848 623/1.15 |
| 2012/0179086 A1* | 7/2012 | Shank | A61F 2/04 604/8 |
| 2012/0290065 A1 | 11/2012 | Li et al. | |
| 2014/0012192 A1 | 1/2014 | Bar-On et al. | |
| 2015/0257908 A1 | 9/2015 | Chao et al. | |
| 2017/0135830 A1 | 5/2017 | Harkin et al. | |

FOREIGN PATENT DOCUMENTS

| | | |
|---|---|---|
| EP | 3167845 A1 | 5/2017 |
| WO | 90/13332 A1 | 11/1990 |
| WO | 2011/021779 A2 | 2/2011 |
| WO | 201102779 A1 | 6/2011 |
| WO | 2015101975 A1 | 7/2015 |
| WO | 2015111063 A1 | 7/2015 |
| WO | 2015138763 A1 | 9/2015 |
| WO | 2017/081326 A2 | 5/2017 |

OTHER PUBLICATIONS

European Search Report, EP 15194391.7, "Implantable Biocompatible Expander Suitable for Treatment of Constrictions of Body Lumen," dated May 24, 2016.
NonFinal Office Action, U.S. Appl. No. 15/351,282, "Implantable Biocompatible Expander Suitable for Treatment of Constrictions of Body Lumen," dated Apr. 24, 2018.
Final Office Action, U.S. Appl. No. 15/351,282, "Implantable Biocompatible Expander Suitable for Treatment of Constrictions of Body Lumen," dated Dec. 17, 2018.
International Preliminary Report on Patentability, PCT/EP2016/077606, entitled "An Implantable Biocompatible Expander Suitable for Treatment of Constrictions of Body Lumen," dated May 15, 2018.
Notice of Allowance for U.S. Appl. No. 15/351,282, entitled "Implantable Biocompatible Expander Suitable for Treatment of Constrictions of Body Lumen," dated Jan. 31, 2020.
Supplemental Notice of Allowance for U.S. Appl. No. 15/351,282, entitled "Implantable Biocompatible Expander Suitable for Treatment of Constrictions of Body Lumen," dated Mar. 24, 2020.
Supplemental Notice of Allowance for U.S. Appl. No. 15/351,282, entitled "Implantable Biocompatible Expander Suitable for Treatment of Constrictions of Body Lumen," dated May 12, 2020.

* cited by examiner

IMPLANTABLE BIOCOMPATIBLE EXPANDER SUITABLE FOR TREATMENT OF CONSTRICTIONS OF BODY LUMEN

This application is the U.S. National Stage of International Application No. PCT/EP2016/077606, filed Nov. 14, 2016, which designates the U.S., published in English, claims priority to EP Application No. 15194391.7, filed Nov. 12, 2015, and claims the benefit of U.S. Provisional Application No. 62/321,639, filed Apr. 12, 2016. The entire teachings of the above applications are incorporated herein by reference.

INTRODUCTION

Benign prostatic hyperplasia (BPH) involves hyperplasia of prostatic stromal and epithelial cells, resulting in formation of large discrete nodules in the transition zone of the prostate gland. When sufficiently large, the nodules impinge on the prostatic urethra and increase resistance to flow of urine from the bladder, causing discomfort for the patient. Resistance to urine flow requires the bladder to work harder during voiding, leading to progressive hypertrophy, instability and weakness of the bladder muscle. Various treatments are available for BPH, including medication such as alpha blockers and 5-reductase inhibitors, clean intermittent self-catheterisation, surgery and minimally invasive therapies such as transurethral microwave thermotherapy and transurethral needle ablation. A further treatment option is to implant a stent within the prostatic urethra. One such stent is described in U.S. Pat. No. 5,269,802 and comprises two rings connected by three struts that maintain the two rings in a co-planar relationship. In use, the larger of the two rings is placed in the bladder and the smaller ring is placed in the prostatic urethra. Prostatic stents can offer immediate relief for symptoms of BPH but they have fallen out of favour due a high rate of side effects. They are usually long cylindrical type stents that resemble traditional stents used in the heart blood vessels or for peripheral vascular disease. They can migrate from their deployment position and travel to the bladder or to the membranous urethra (up to 12.5% of patients), encrust and block urethra (up to 27.5%), cause incontinence (up to 3%) and pain. Cases of a profound inflammatory response to prostatic stents have been reported. In total, these combined side effects have historically resulted in 8% to 47% of prostatic stents to be removed. In addition, these previous prostatic stents have not had designs which accommodate the unique characteristics of the prostatic urethra.

WO2015/138763 describes urethral expanders configured for implantation into the prostatic urethra and in-situ expansion and comprising a number of spaced apart interconnected circular ring. This device suffers from a number of drawbacks including: increased encrustation due to the circumferential disposition of the rings meaning that they will meet the urine at 90°, difficulty in removal due to the rings being embedded at 90° to the longitudinal axis of the urethra; the rings impinging on the verumontanum which may block some of the ejaculatory and prostatic ducts; the rigidity and static nature of the ring solution impeding the natural movements of the prostatic urethra during urination and ejaculation and causing pain; and the spaced-apart nature of the rings which effects non-continuous expansion along the length of the prostatic urethra.

It is an object of the invention to overcome at least one of the above-referenced problems.

STATEMENTS OF INVENTION

Broadly, the invention provides a resiliently deformable expander that in one embodiment is suitable for the treatment of benign prostatic hyperplasia (BPH). The expander generally takes the form of a single elongated undulating ring that is configured for implantation into a body lumen at a target locus that is constricted due to adjacent diseased tissue. The undulating ring has at least two distal prongs and at least two proximal prongs that are typically configured for invagination into the wall of the body lumen. The expander is typically resiliently deformable in a radial direction between a contracted orientation suitable for transluminal delivery to the target site through the body lumen and an expanded (deployed) orientation configured to effect in-situ dilation of the body lumen at the target site. The elongated undulating ring configuration provides minimal contact area between the stent and the wall of the body lumen, thereby reducing the extent of potential encrustation. Further, the struts of the undulating ring, due to the elongated undulating ring shape, extend substantially longitudinally (as opposed to circumferentially) thereby ensuring that flow of fluid is along the struts as opposed to at right angles to the struts for the majority of the exposed surface area. This further reduces the incidence of encrustation. The substantially longitudinal nature of the struts will also facilitate easier removal. Furthermore, the undulating ring configuration of the expander allows for differential flexing of the expander during use, thus allowing the shape of the mirror the anatomical shape, and adhere to, and move with, the shape of the wall of the body lumen. In particular, the expander of the invention does not disrupt the Verumontanum and ejaculatory ducts and its proximal three projections sit anatomically in the triangularly shaped distal urethra making migration less likely (as well as facilitating removal). The undulating ring configuration also ensures that expansion occurs in the correct anatomical zone of the urethra (in particular, pushing against the transition zone of the prostate).

The expander of the invention provides a means of dilating a body lumen that has been constricted due to, for example, a pathological state or due to trauma. One example of a pathology is benign prostatic hyperplasia, a proliferative disease of the prostate gland that causes the prostate to constrict around, and partially block, the prostatic urethra. Thus, in one embodiment, the invention provides a resiliently deformable expander for the treatment of benign prostatic hyperplasia (BPH), where the expander takes the form of an undulating (and preferably sinusoidal) ring that is configured for implantation into the prostatic urethra between the bladder neck and external sphincter, that in one embodiment substantially spans the prostatic urethra between the bladder neck and external sphincter. In this embodiment, the undulating ring preferably has at least three distal prongs and at least three proximal prongs that are suitably configured for invagination into the wall of the prostatic urethra, and is ideally resiliently deformable from a relaxed radially expanded orientation to a radially contracted orientation suitable for transurethral delivery to a target locus, and when in-situ causes dilation of the prostatic urethra allowing urine to pass freely through the prostatic urethra thereby addressing a symptom of BPH. In addition, the undulating ring configuration of the expander provides minimal contact area between the expander and the wall of the prostatic urethra, thereby minimising risk of the stent obstructing the ejaculatory ducts, and also reducing the extent of encrustation. The undulating ring configuration also allows for the proximal stent to fit securely in the distal urethra with the expander's triangular cross sectional shape matching the triangular cross sectional shape of the urethra (with each prong sitting in the most lateral triangular recesses of the urethra. Furthermore, the undulating ring configuration of the expander allows for differential flexing of the expander during use, thus allowing the shape of the expander adhere to, and move with, the shape of the wall of the wall of the prostatic urethra during exposure to the different forces experienced during urination and ejaculation. (i.e. expansion of the urethra during urination and contraction/spasm of both the bladder neck and the distal urethra/external sphincter during ejaculation). The location of the prongs in the triangular recesses will also allow for normal movement of the urethral wall during contraction.

Accordingly, in a first aspect, the invention provides an implantable expander suitable for implantation into a body lumen and dilation of a constricted section of the body lumen, the expander comprising an undulating ring that is typically elongated and comprising at least two proximal prongs and at least two distal prongs, wherein the expander is typically resiliently deformable and ideally self-expandable from a radially contracted orientation suitable for transluminal delivery through the body lumen to a radially expanded orientation, wherein the expander is configured to span a substantial part of the constricted section of the body lumen and cause in-situ expansion of the substantial part of the constricted section of the body lumen.

The implantable biocompatible expander of the invention is suitable for treatment of constrictions of various types of body lumen, including urinary ducts (such as a urethra or ureter), the oesophagus and the gastrointestinal tract. Constrictions may be caused by various pathologies, including benign and malignant proliferative disorders of the adjacent tissue. In a preferred embodiment, the expander is configured for use with a urinary duct, for example to dilate a urinary duct that has been constricted due to growth in the urinary duct or an adjacent tissue.

In one embodiment, the invention provides an implantable biocompatible expander suitable for implantation into a urinary duct and dilation of a constricted section of the urinary duct, the expander comprising an elongated undulating ring comprising at least two proximal prongs and at least two distal prongs, wherein the expander is resiliently deformable and self-expandable from a radially contracted orientation suitable for transluminal delivery through the urinary duct to a radially expanded orientation, wherein the expander is configured to span a substantial part of the constricted section of the urinary duct and cause in-situ expansion of the substantial part of the constricted section of the urinary duct.

The expander of the invention is particularly suitable for treatment of benign prostatic hyperplasia (BPH). Thus, in one embodiment, the invention provides a provides an implantable biocompatible expander according to the invention that is suitable for treatment of benign prostatic hyperplasia, wherein the expander is configured for implantation into the prostatic urethra between, and spanning a substantial section of, the prostatic urethra between, the bladder neck and external sphincter, and wherein the expander is resiliently deformable and self-expandable from a radially contracted orientation suitable for transluminal delivery through the urethra to a radially expanded orientation.

Preferably, the distal prongs and/or the proximal prongs are configured for invagination into the wall of the prostatic urethra, In one embodiment, the elongated undulating ring comprises at least three proximal prongs and at least three distal prongs.

In one embodiment, the undulating ring comprises three or five distal prongs and three or five proximal prongs.

In one embodiment, the undulating ring comprises three distal prongs and three proximal prongs. When the indication to be treated is BPH, the use of three distal and proximal prongs is ideal as the expander will have a substantially triangular cross-section which matches the cross section of the prostatic urethra.

In one embodiment, the undulating ring comprises five distal prongs and five proximal prongs.

In one embodiment, the undulating ring comprises seven distal prongs and seven proximal prongs.

In one embodiment, the undulating ring is a sinusoidal ring.

The undulating ring typically comprises elongated struts connecting the distal and proximal prongs and open areas between the struts and prongs. Suitably the radially outwardly facing surface of the prongs and struts is less than 10% of the total open areas. Suitably the radially outwardly facing surface of the prongs and struts is less than 7% of the total open areas. Suitably the radially outwardly facing surface of the prongs and struts is less than 5% of the total open areas. Suitably the radially outwardly facing surface of the prongs and struts is less than 3% of the total open areas.

In one embodiment, the prongs are substantially V-shaped. In another embodiment, the prongs are substantially U-shaped. In another embodiment, the prongs are substantially rectangular shaped.

In one embodiment, the elongated struts of each prong are substantially straight. In another embodiment, the elongated struts of each prong are substantially curved. In one embodiment, the elongated struts of each prong are curved substantially outwardly. In one embodiment, the elongated struts of each prong are curved substantially outwardly. In one embodiment, at least one elongated strut is curved substantially outwardly and at least one elongated strut is curved substantially inwardly.

In one embodiment of the invention, an apex of one of more of the prongs comprises a loop or lip. Typically, the loop or lip projects radially into the expander (i.e. the ends of the prongs flare inwardly). In another embodiment, the loop or lip projects radially out of the expander (i.e. the ends of the prongs flare inwardly).

In one embodiment, the apices of the distal prongs are unconnected circumferentially. In one embodiment, the apices of the proximal prongs are unconnected circumferentially.

In one embodiment, the prongs are longitudinally staggered with respect to each other. In one embodiment, the prongs are longitudinally staggered with respect to each other at a distal end of the expander. In another embodiment, the prongs are longitudinally staggered with respect to each other at a proximal end of the expander. In another embodiment, the prongs are longitudinally staggered with respect to each other at both ends of the expander.

In one embodiment, an apex of the distal prongs comprises a loop or lip that projects generally radially into the expander and an apex of the proximal prongs comprises a loop or lip that projects generally radially out of the expander. In another embodiment, an apex of the distal prongs comprises a loop or lip that projects generally radially out of the expander and an apex of the proximal prongs comprises a loop or lip that projects generally radially into the expander.

In one embodiment of the invention, an apex of one of more of the prongs is substantially M-shaped.

In one embodiment, the expander is formed from a wire, for example nitinol wire. The wire can have any profile, for example circular, oval, rectangular, square, or otherwise. In a preferred embodiment, the profile is circular. The expander may also be formed by a ribbon. Also, it can be formed by any process, for example cutting from a tubular structure. In a preferred embodiment, the expander is formed by laser cutting. In one embodiment, the expander comprises an anchoring element for anchoring the expander in-situ within a body lumen. In one embodiment, the expander comprises at least two anchoring elements. In one embodiment, the at least two anchoring elements project in different directions. In one embodiment, the expander comprises at least one anchoring element disposed at a proximal end of the expander and at least one anchoring element disposed at a distal end of the expander. In one embodiment, the anchoring element comprises a projection, for example a hook, barb, coil, or screw. In one embodiment of the invention the undulating or sinusoidal ring comprises a single wire, typically having ends that are joined at or close to each end. In one embodiment of the invention, one of the ends of the wire is shaped to form the anchoring element. In one embodiment of the invention, the anchoring element comprises an end of the wire that extends beyond a joining point. In one embodiment of the invention, each end of the wire extends beyond a joining point, typically co-extensive with the strut of the expander. In one embodiment, the or each anchoring element, or at least a part thereof, is biodegradable. This allows the anchoring element (or a part thereof) biodegrade over time, allowing for ease of removal after the anchoring element has degraded.

In one embodiment, the anchoring element comprises a collar that is configured to embrace a strut and one or more projections extending from the collar. In one embodiment, the projections are disposed on each end of the collar. In one embodiment, projections are disposed on opposite sides of the collar. In one embodiment, the or each projection is a barb.

In one embodiment, the elongated sinusoidal ring is cylindrical, conical, frusto-conical, tapers inwardly at each end (i.e. barrel shaped), or tapers inwardly towards in mid-section (i.e. has a waist).

In one embodiment, the expander is adapted to elute a pharmaceutically active agent. Examples of pharmaceutically active agents include tissue growth inhibitors such as alpha reductase inhibitors or cell proliferation inhibitors such as paclitaxel. Methods of incorporating drugs into the expander for in-vivo elution will be apparent to a person skilled in the art and are described in, for example, U.S. Pat. Nos. 5,591,277, 5,697,967, 5,599,325, US2007/0077266, WO0112779 and WO9013332.

In another aspect, the invention provides an implantable biocompatible expander to treat BPH, wherein the expander:
  is configured for resilient deformation and self-expansion from a radially contracted orientation suitable for transluminal delivery through a urinary duct (in particular through a urethra) to a radially expanded orientation capable of effecting in-situ dilation of the prostatic urethra;
  is typically configured to fit within the prostatic urethra between the bladder neck and the external sphincter without blocking the verumontanum;
  is typically configured to anatomically conform to the wall of prostatic urethra; and typically comprises a plurality of longitudinal struts and is typically free of circumferential struts.

In another aspect, the invention provides an elongated, indwelling, expander ring to treat BPH, the expander ring configured to fit within the prostatic urethra between the bladder neck and the external sphincter without blocking the verumontanum and effect in-situ dilation of the prostatic urethra.

In another aspect, the invention provides an elongated, indwelling, expander ring to treat BPH, the expander ring comprising a plurality of longitudinal struts and typically no circumferential struts configured to allow the expander conform to the anatomy of the prostatic urethra when expanded without blocking the verumontanum.

In one embodiment, the distal end of the expander is configured to engage the wall of the distal prostatic urethra without obstructing the verumontanum.

In one embodiment, the longitudinal struts on a distal end of the expander are configured to engage the wall of the distal prostatic urethra without obstructing the verumontanum.

In one embodiment, the proximal end of the expander is configured to engage the wall of the proximal prostatic urethra adjacent the transition zone of the prostate gland.

In one embodiment, the longitudinal struts on a proximal end of the expander are configured to engage the wall of the proximal prostatic urethra adjacent the transition zone of the prostate gland.

In one embodiment, the longitudinal struts are configured for differential flexing of the expander during use (differential flexing of the distal and proximal ends of the expander), thus allowing the shape of the expander adhere to, and move with, the shape of the wall of the body lumen.

In one embodiment, the longitudinal struts are formed by an undulating structural element, for example a sinusoidal structural element. In one embodiment, the structural element is a wire or a ribbon, for example a metal wire or ribbon.

In one embodiment, the expander comprises an elongated ring. In one embodiment, the elongated ring is formed from an undulating structural element, typically a single undulating structural element. In one embodiment, the elongated ring is formed from expansible mesh.

In another aspect, the invention provides a delivery device for an expander of the invention comprising a handle operatively connected to a delivery tube having a hollow distal end remote from the handle configured to receive an expander of the invention in a contracted orientation, and an ejection element operatively connected to the handle and operable to eject the expander from the open end of the delivery tube. In one embodiment, the delivery tube is configured for insertion into the urethra through the penis and for delivery of an expander of the invention into the prostatic urethra. In another embodiment, the delivery tube is configured for insertion into the oesophagus through the mouth and for delivery of an expander of the invention into the oesophagus. In another embodiment, the delivery tube is configured for insertion into the colon through the anus and for delivery of an expander of the invention into the colon. In one embodiment, the ejection element comprises a head configured to engage a proximal end of the expander. This allows the ejection element grip the expander and effect movement of the expander proximally (towards the handle—retraction) and distally (away from the handle—ejection). In one embodiment, the head of ejection element comprises a jig configured to engage the apex of at least one of the proximal prongs. In one embodiment, the head of ejection element comprises a jig configured to engage the apex of all of the proximal prongs, for example two, three, five or seven proximal prongs. In one embodiment, the head of the ejection element is configured to extend into a lumen of the proximal end of the expander. In one embodiment, the head of the ejection element has a cross-sectional area that matches the cross-sectional area of the body lumen of the lumen into which the expander is to be inserted. This, when the expander is radially contracted and inserted into the open end of the delivery tube, the head of the ejection element is inserted into the lumen of the proximal end of the expander, forcing the expander to assume the cross-sectional shape of the head. In the case of the prostatic urethra, the head of the ejection element typically has a substantially triangular cross section, and this forces the expander to assume a generally triangular cross-sectional shape, substantially matching the cross-sectional shape of the prostatic urethra. In one embodiment, the head of the ejection element has a substantially pentagonal cross section. In one embodiment, the head of the ejection element has a substantially heptagonal cross section.

In one embodiment, the delivery device comprises an imaging device disposed within the hollow distal end of the delivery tube and configured for imaging the placement of the expander. In one embodiment the imaging device is disposed within a lumen of the delivery tube. In one embodiment the imaging device is disposed concentrically within the lumen of the delivery tube. In one embodiment, the imaging device comprises a light source configured to illuminate, in use, a part of the body lumen adjacent the end of the delivery device. In one embodiment, the imaging device is a cystoscope.

In another aspect, the invention relates to a method of treating a disease or condition characterised by constriction of a body lumen in a mammal, which method employs an implantable expander (typically an implantable expander of the invention), the method comprising the steps of implanting the expander into a constricted section of the body lumen, whereby the expander in the expanded orientation effects in-situ dilation of the constricted section of the body lumen.

In one embodiment, the method comprises the steps of:
delivering the expander in a radially contracted orientation through the body lumen to a target location within the body lumen characterised by a constricted section of the body lumen; and
allowing the expander expand at the target location to a radially expanded orientation against the wall of the body lumen, whereby the expander in the expanded orientation effects in-situ dilation of the constricted section of the body lumen.

In one embodiment, the disease or condition characterised by constriction of a body lumen in a mammal is a proliferative disease of the urethra.

In one embodiment, the proliferative disease of the urethra is benign prostatic hyperplasia.

In one embodiment, the expander is configured for resilient deformation and self-expansion from a radially contracted orientation suitable for transluminal delivery through a urinary duct to a radially expanded orientation capable of effecting in-situ dilation of the prostatic urethra In one embodiment, the method of the invention employs a delivery device configured to hold the expander in a radially contracted orientation, deliver the expander through the body lumen to the constricted section of the body lumen in the radially contracted orientation, and release the expander at the constricted section of the body lumen.

In one embodiment, the delivery device comprises a handle including actuation means configured to remotely release the expander, in which the method includes a step of actuating the actuation means of the delivery device to remotely release the expander at the target location within the prostatic urethra.

In one embodiment, the method of the invention additionally employs an imaging device suitable for providing an image of the constricted section of the body lumen, the method comprising the using the imaging device to correctly position the expander at the constricted section of the body lumen.

In one embodiment, the positioning step comprising longitudinal adjustment of the position of the expander within the body lumen.

In one embodiment, the positioning step comprising radial adjustment of the position of the expander within the body lumen.

In one embodiment, the delivery device comprises a light at a distal end thereof, wherein the step of delivering the expander to the target location includes a step of guiding the delivery device and expander to the target location in the body lumen by external monitoring of the position of the light.

In one embodiment, the expander is an expander according to the invention.

In another aspect, the invention relates to a method of treating benign prostatic hyperplasia in a mammal, which method employs an implantable biocompatible expander configured for resilient deformation and self-expansion from a radially contracted orientation suitable for transluminal delivery through a urinary duct to a radially expanded orientation capable of effecting in-situ dilation of the prostatic urethra, wherein the expander is configured to fit within the prostatic urethra between the bladder neck and the external sphincter, the method comprising the steps of implanting the expander into the prostatic urethra at a target location between the bladder neck and the external sphincter, whereby the expander in the radially expanded orientation effects in-situ dilation of the prostatic urethra between the bladder neck and the external sphincter.

In one embodiment, the method comprises the steps of:
delivering the expander in a radially contracted orientation through the urethra to the target location within the prostatic urethra between the bladder neck and the external sphincter; and
allowing the expander expand at the target location to a radially expanded orientation against the wall of the prostatic urethra.

In one embodiment, the expander is configured to effect in-situ dilation of the prostatic urethra at the target location without blocking the verumontanum.

In one embodiment, the expander is configured to fit in the prostatic urethra between the bladder neck and the external sphincter without inhibiting the function of the bladder neck.

In one embodiment, the expander is configured to fit in the prostatic urethra between the bladder neck and the external sphincter without inhibiting the function of the bladder neck and the external sphincter.

In one embodiment, the expander is configured to anatomically conform to the wall of the prostatic urethra.

In one embodiment, the expander is resiliently deformable to conform to the wall of the prostatic urethra as the shape and topography of the wall changes during, for example, urination or ejaculation.

In one embodiment, the method of the invention employs a delivery device configured to hold the expander in a radially contracted orientation, deliver the expander through the urethra to the prostatic urethra in the radially contracted orientation, and release the expander in the prostatic urethra whereby upon release the expander self-expands to the radially expanded orientation.

In one embodiment, the delivery device comprises a handle including actuation means configured to remotely release the expander, in which the method includes a step of actuating the actuation means of the delivery device to remotely release the expander within the prostatic urethra.

In one embodiment, the expander is configured to span a substantial section of the prostatic urethra between the bladder neck and the external sphincter.

In one embodiment of a method of the invention, the expander is configured to anatomically conform to the lumen of the prostatic urethra.

In one embodiment, the expander is configured to dilate the prostatic urethra without blocking the verumontanum. For example, the expander may comprise a configuration of struts that provides an opening dimensioned to overlap with the verumontanum.

In one embodiment, the expander has a longitudinal dimension of 15 mm to 35 mm.

In one embodiment, the delivery device comprises a light at a distal end thereof, wherein the step of delivering the expander to the prostatic urethra includes a step of guiding the delivery device by external monitoring of the position of the light, such that the expander is located between the bladder neck and the external sphincter.

In one embodiment, the implantable expander is an implantable expander of the invention.

In one embodiment, the implantable expander employed in the method of the invention comprises a hollow lumen and is configured for resilient deformation and self-expansion from a radially contracted orientation suitable for transluminal delivery through the urinary duct to a radially expanded orientation, wherein the expander is configured to fit within the prostatic urethra between the bladder neck and the external sphincter and span a substantial section of the prostatic urethra without blocking the verumontamum, the method comprising the steps of:

delivering the expander in radially contracted orientation through the urethra to a target location within the prostatic urethra between the bladder neck and the external sphincter; and allowing the expander expand at the target location to a radially expanded orientation against the wall of the prostatic urethra, whereby the expander in the expanded orientation effects in-situ dilation of the prostatic urethra at the target location without blocking the verumontanum and preserves the function of the bladder neck.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

"Implantable" as applied to an expander of the invention means a device that is formed of materials that are biocompatible, i.e. do not normally promote an immune response in the host and/or cause trauma, inflammation or scarring. Examples of such materials include gold, titanium, cobalt-chromium alloy, tantalum alloy, nitinol, and several polymers.

"Expander" means a biocompatible device having a lumen to allow for flow of liquid past the expander and that is resiliently deformable and self-expandable between a relaxed, expanded orientation and a contracted orientation suitable for transluminal delivery, and sometimes percutaneous delivery, whereby when in-situ the expander exerts an outward radial force against the walls of the body lumen. The expander usually take a generally cylindrical form and may be configured to conform to the shape of a section of a body lumen. Expanders for body lumen such as arteries, veins and urethras are known in the literature, for example WO2015138763, CN202822454, and U.S. Pat. No. 5,269,802. The expander may be made from any suitable material for example stainless steel, a shape memory polymer (for example a linear block copolymer or other thermoplastic polymers having shape memory effect), and a shape memory alloy (i.e. nitinol).

"Body lumen" means an elongated tubular organ within the body, including urinary ducts, gastrointestinal tract, oesophagus, and vasculature. "Urinary duct" means a urethra or ureter.

"Undulating ring" means a ring-shaped device formed from a structural element such as a wire shaped in a wave-like form and having at least two distal prongs and at least two proximal prongs (see FIGS. 1 to 24). The undulating structural element may take a substantially sinusoidal wave form (a sinusoidal ring), a substantially square wave form (a square wave ring), a wave form that is intermediate a sinusoidal wave form and square wave form, and any combination of these wave forms. In one embodiment, the undulating ring has a substantially periodic wave form. In one embodiment, the undulating ring has a non-periodic wave form. In one embodiment, the prongs are substantially V-shaped. In one embodiment, the prongs are substantially rectangular shaped. In a preferred embodiment, the undulating ring is a sinusoidal ring. In a preferred embodiment, the undulating ring has three distal prongs and three proximal prongs. An undulating ring having three distal and proximal prongs is particularly suitable for treatment of benign prostatic hyperplasia. In one embodiment, at least one of the prongs forms two or more sub-prongs, for example a prong may be W-shaped to form two sub-prongs. In one embodiment, the undulating ring has a width (in a relaxed state) that is greater than the width of the diseased prostatic urethra. In one embodiment, the undulating ring has a width (in a relaxed state) that is 5-40% greater than the width of the diseased prostatic urethra. In one embodiment, the undulating ring has a width (in a relaxed state) that is 10-30% greater than the width of the diseased prostatic urethra.

"Elongated undulating ring" means an undulating ring that has a longitudinal dimension that is equal to or greater than its maximal transverse dimension when in a relaxed, expanded, state. Typically, the maximal longitudinal dimension is greater than its maximal transverse dimension when in a relaxed, expanded, state. Generally, the undulating ring has a length of 10-45 mm. Typically, the undulating ring has a width (in a relaxed state) of 6-30 mm. In one embodiment, the undulating ring has a length of 15-25 mm. In one embodiment, the undulating ring has a width (in a relaxed state) of 10-20 mm. In one embodiment, the length of the undulating ring is at least 10% greater than the width of the undulating ring (in a relaxed state). In one embodiment, the length of the undulating ring is at least 20% greater than the width of the undulating ring (in a relaxed state). In one embodiment, the length of the undulating ring is at least 30% greater than the width of the undulating ring (in a relaxed state). In one embodiment, the length of the undulating ring is at least 40% greater than the width of the undulating ring (in a relaxed state). In one embodiment, the length of the undulating ring is 1-40% greater than the width of the undulating ring (in a relaxed state). In one embodiment, the length of the undulating ring is 5-40% greater than the width of the undulating ring (in a relaxed state). In one embodiment, the length of the undulating ring is 5-30% greater than the width of the undulating ring (in a relaxed state). In one embodiment, the length of the undulating ring is 5-20% greater than the width of the undulating ring (in a relaxed state).

"Proximal prongs" refers to the prongs that are disposed at the delivery side of the body lumen when the expander is in-situ within the body lumen. "Distal prongs" refers to the prongs that are disposed opposite to the delivery side of the body lumen when the expander is in-situ within the body lumen. In the case of an extender of the invention for that is configured for treatment of BPH, the proximal prongs will typically lie adjacent to the external sphincter, and the distal prongs will typically lie adjacent to the bladder neck.

"Resiliently deformable and self-expandable" means that the expander can be radially compressed into a contracted orientation (suitable for transluminal delivery) and upon release of the compression forces will assume a relaxed expanded orientation. In this manner, the expander is delivered using a suitable delivery vehicle in a contracted orientation and the compression forces are released in-situ at a target site allowing the expander exert outward radial forces against the wall of the body lumen. Generally, the width of the expander in the relaxed state is greater than the width of the target body lumen. Various delivery means are suitable, for example a delivery tube having a hollow tip dimensioned to receive and hold the expander in a contracted orientation, whereby upon ejection from the delivery tube the expander expands. Other delivery means include a catheter having an outer sheath that during delivery embraces the expander and when in-situ is withdrawn allowing the expander expand. In one embodiment, the expander can be contracted to a cross-sectional area of less than 50% of the cross-sectional area of the expander in its relaxed state. In one embodiment, the expander can be contracted to a cross-sectional area of less than 40% of the cross-sectional area of the expander in its relaxed state. In one embodiment, the expander can be contracted to a cross-sectional area of less than 30% of the cross-sectional area of the expander in its relaxed state. In this regard, "cross-sectional area" means a cross-section area taken through a mid-point of the expander and defined by the longitudinal struts.

"Radially contracted orientation suitable for transluminal delivery" means that the expander is radially contracted to bring the prongs close together thereby significantly reducing the transverse profile of the ring such that it can be delivered through the body lumen.

"Relaxed radially expanded orientation" means that the profile of the expander when it is in a relaxed state.

"Substantial section of the prostatic urethra" means at least 30% of the length of the prostatic urethra between the bladder neck and external sphincter. In one embodiment, the undulating ring is configured to span at least 40% of the length of the prostatic urethra between the bladder neck and external sphincter. In one embodiment, the undulating ring is configured to span at least 50% of the length of the prostatic urethra between the bladder neck and external sphincter. In one embodiment, the undulating ring is configured to span at least 60% of the length of the prostatic urethra between the bladder neck and external sphincter. In one embodiment, the undulating ring is configured to span at least 70% of the length of the prostatic urethra between the bladder neck and external sphincter.

"Self-expansion" as applied to the resiliently deformable expander means that the expander is adjustable between a radially expanded and a radially contracted configuration and biased into the radially expanded configuration.

"Disease or condition characterised by constriction of a body lumen in a mammal" means for example proliferative conditions such as benign prostatic hyperplasia, or other proliferative or non-proliferative conditions such as inflammation, associated with a body lumen and which cause constriction or mis-shaping, and partial or complete blockage of the body lumen. In one embodiment the body lumen is a body lumen of the renal system, for example a urethra or ureter. In one embodiment, the mammal is a human for example a male human or a female human. In one embodiment, the condition is inflammation of the body lumen. In one embodiment, the condition is inflammation of the ureter or urethra (for example caused by trauma or a renal stone). In one embodiment, the condition is incontinence, for example stress urinary incontinence. In this embodiment, the expander is generally placed in the urethra between the bladder neck and the external sphincter (typically for the purpose of re-shaping the prostatic urethra).

"Target location" as applied to a method of treating benign prostatic hyperplasia means a section of the prostatic urethra between the bladder neck and the external sphincter that spans a substantial section of the prostatic urethra including a constricted section. Typically, the target location is spaced at least 5 mm from both the external sphincter and the bladder neck. Typically, the target location is spaced at least 10 mm from both the external sphincter and the bladder neck.

"Without inhibiting the function of the bladder neck" as applied to the expander means that the expander when correctly positioned in the prostatic urethra between the bladder neck and the external sphincter does not affect the functioning of the bladder neck allowing the neck open and close in a normal manner during urination and tonically contract during ejaculation.

"Without inhibiting the function of the external sphincter" as applied to the expander means that the expander when correctly positioned in the prostatic urethra between the bladder neck and the external sphincter does not affect the functioning of the external sphincter allowing the sphincter to rhythmically contract/spasm during ejaculation. This is the muscle that propels the ejaculate in the normal antegrade fashion (the spasm of the external sphincter in conjunction with the tight closing of the bladder neck means the ejaculate is propelled forward to the penis).

"Verumontanum" (or seminal colliculus) is a distinctive median elevation on the posterior wall of the prostatic urethra. It is an important landmark as it contains the slit-like openings of the ejaculatory ducts (containing semen) and the openings of the prostatic ducts (containing prostatic fluid).

"Without blocking the nerumontanum" as applied to the expander means that the expander is configured such that when it is deployed in an expanded orientation within the prostatic urethra between the bladder neck and external sphincter it does not block the verumontanum and lessens or completely avoids disruption, compression or damage of the Verumontanum that can cause dysfunction in emission of semen into the prostatic urethra.

"Imaging device" means a device that can remotely image the urethra from outside the body. Examples include ultrasound and CT scanners.

"Anatomically conform" as applied to the expander means that the expander is configured to confirm to the wall of the prostatic urethra. In one embodiment, it means that the expander is deformable to conform to the wall of the prostatic urethra as the shape and topography of the wall changes during, for example, urination or ejaculation.

BRIEF DESCRIPTION OF THE FIGURES

The invention will be more clearly understood from the following description of some embodiments thereof given by way of example only with reference to the accompanying figures in which.

DETAILED DESCRIPTION OF THE INVENTION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Figure 1:
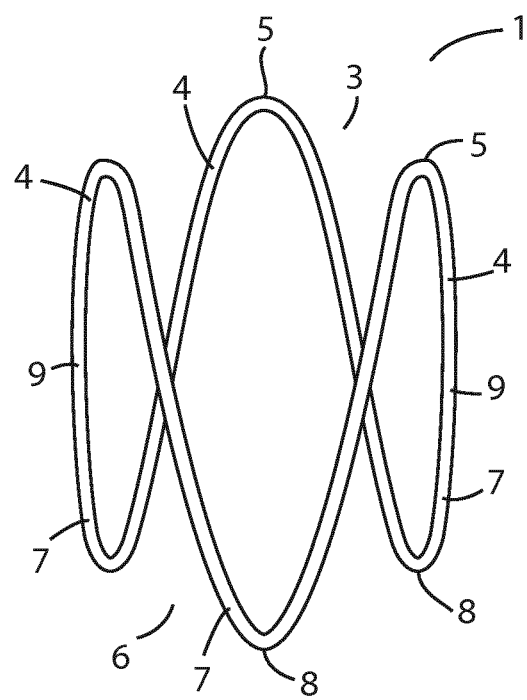
FIG. 1 is an elevational view of a three-prong expander of the invention in a relaxed, expanded, state.

Referring to the drawings, and initially to FIG. 1, there is illustrated an expander according to the invention indicated generally by the reference numeral 1. The expander 1 comprises a single nitinol wire configured as an elongated sinusoidal ring having a distal end 3 comprising three distal prongs 4 with apices 5 and a proximal end 6 having three proximal prongs 7 with apices 8. The prongs are connected by longitudinal struts 9. The expander 1 is shown in an expanded, relaxed, state and has a length of approximately 22 mm and a width of approximately 15 mm. In the expanded state shown, the distance between the apices 5 of adjacent distal prongs 4 at the distal end 3 of the expander is approximately 14 mm. Likewise, the distance between the apices 8 of adjacent proximal prongs 7 at the proximal end 6 of the expander is approximately 14 mm. The nitinol wire has a cross-sectional diameter of approximately 0.4 mm.

Figure 2:
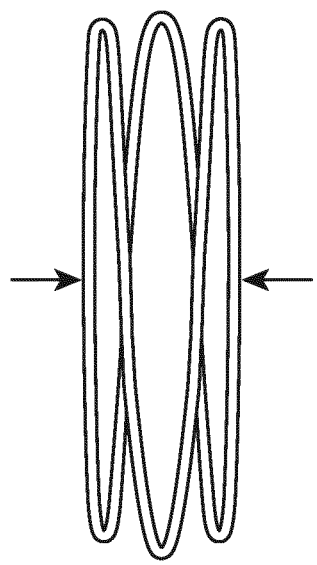
FIG. 2 is an elevational view of a three-prong expander of FIG. 1 in a contracted state.

Referring to FIG. 2, the expander 1 is shown in a radially contracted state in which the distal and proximal prongs are brought together. In this contracted state, the cross-sectional area of the expander is reduced by more than 70% compared with the relaxed expanded state shown in FIG. 1, and the distance between adjacent distal and proximal prongs has reduced from 14 mm to 4-5 mm. In this contracted configuration, the resilient deformability of the sinusoidal ring configuration causes the ring to exert an outward radial force.

Figure 3:
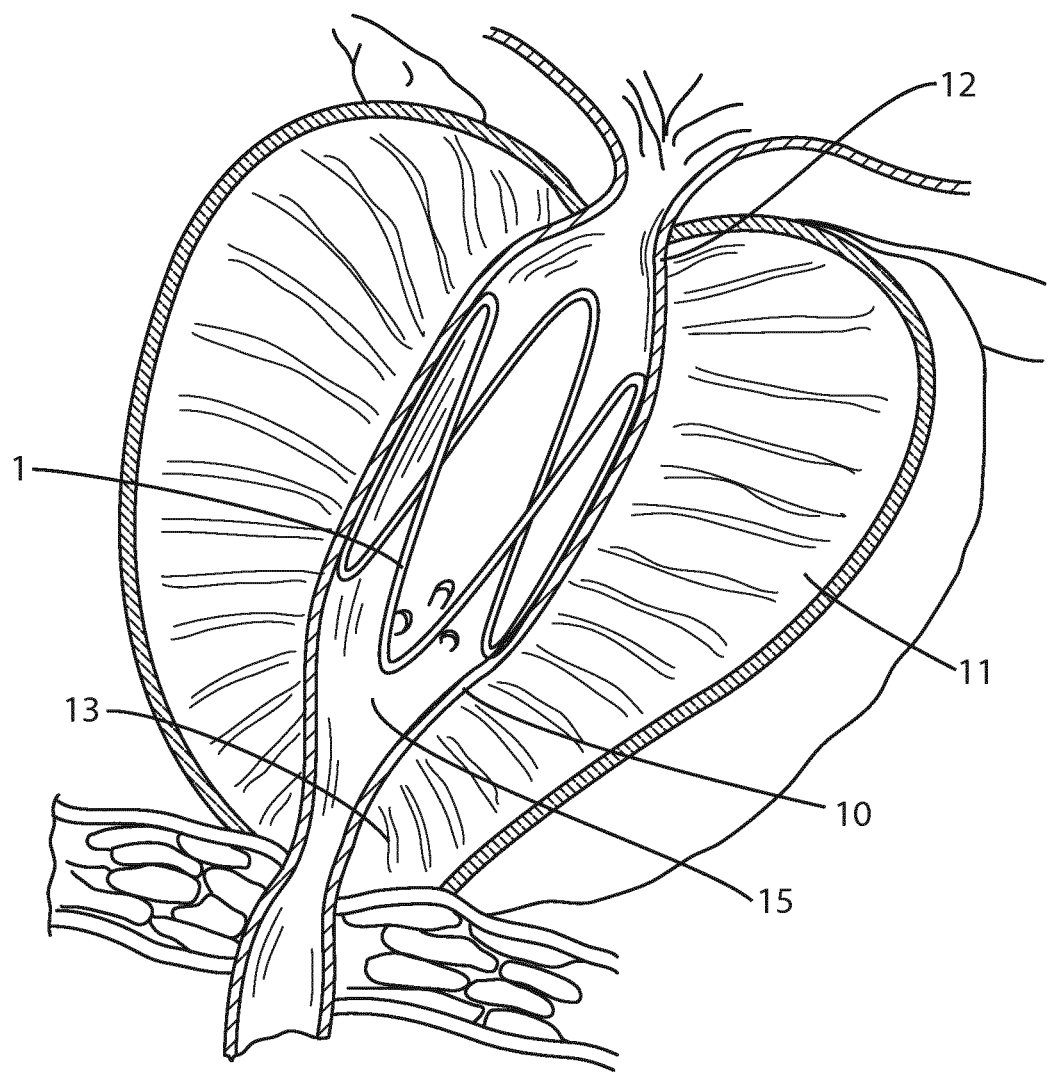
FIG. 3 is a partly sectional view of the expander of FIG. 1 disposed within the prostatic urethra of a patient with benign prostatic hyperplasia in which the expander is exerting an outward radial pressure on the walls of the prostatic urethra causing dilation.
Figure 4:
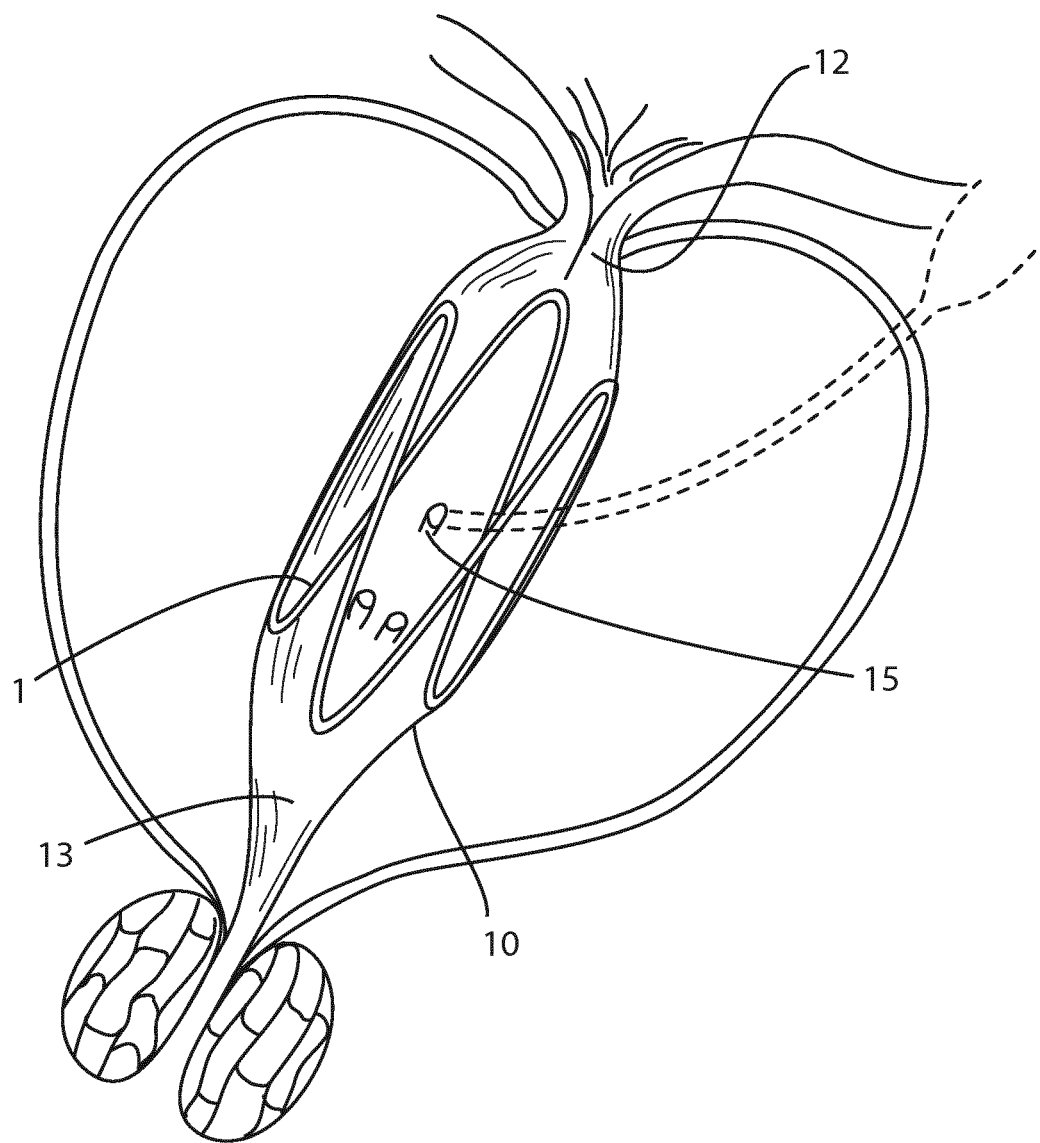
FIG. 4 is a partly sectional view similar to FIG. 2 showing the seminal vesicle and an ejaculatory duct entering the prostatic urethra.

Referring to FIGS. 3 and 4 there is illustrated an expander of FIG. 1 shown in use in the treatment of benign prostatic hyperplasia. The expander 1 is disposed within the prostatic urethra 10 within the prostate gland 11 in between the bladder neck 12 and the external sphincter 13. In this position, the expander 1 exerts an outward radial force against the walls of the prostatic urethra 10 expanding the urethra to allow flow of urine. Due to the sinusoidal ring design, the outward radial force is greatest at each end of the expander, adjacent the transition zones of the prostatic urethra, where the greatest amount of diseased tissue is located. In addition, due to the design of the expander, the contact area between the struts and prongs of the expander and the wall of the prostatic urethra is minimised so that the seminal ducts 15 are not obstructed by the walls of the expander. In addition, as the expander does not have any circumferential struts, removal of the expander is facilitated.

Figure 5:
FIG. 5 is a photograph of an expander of the invention in-situ within a prostatic urethra showing the three proximal prongs and three distal prongs.

FIG. 5 is a picture of the expander of the invention inserted into the prostatic urethra of a cadaver, showing the proximal end of the expander in the foreground and the distal end of the expander in the background abutting the bladder neck. The picture illustrates how the struts of the expander are invaginated into the wall of the prostatic urethra.

Figure 6:
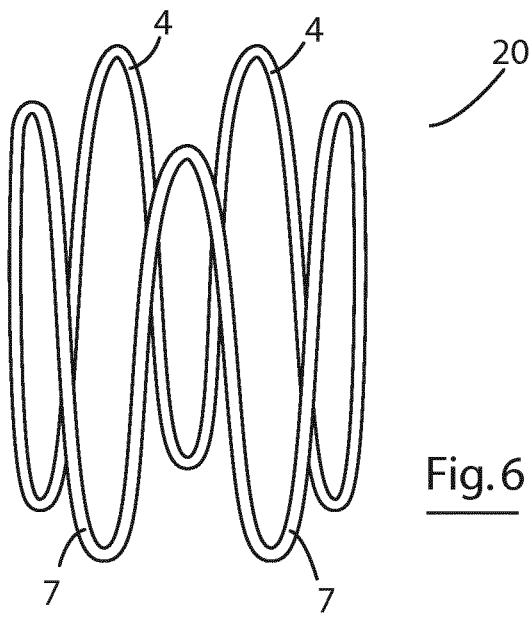
FIG. 6 is an elevational view of a five-prong expander according to the invention.

Referring to FIG. 6, there is illustrated an elevational view of an expander according to an alternative embodiment of the invention in which parts described with reference to the previous embodiments are assigned the same reference numerals. In this embodiment, the expander 20 has five distal prongs 4 and five proximal prongs 7, and the use of this embodiment is the same as that described with reference to the previous embodiment.

Figure 7:
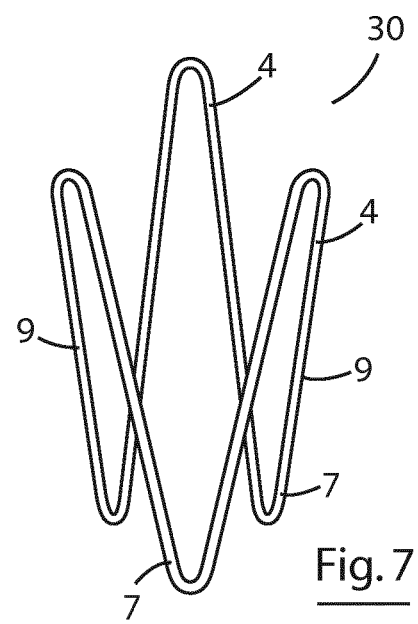
FIG. 7 is an elevational view of a three prong expander according to the invention comprising a tapered sinusoidal ring.

Referring to FIG. 7, there is illustrated an elevational view of an expander according to an alternative embodiment of the invention in which parts described with reference to the previous embodiments are assigned the same reference numerals. In this embodiment, the expander 30 has three distal prongs 4 and three proximal prongs 7, and is longitudinally inwardly tapered towards the distal end 3 with the struts having an angle of between 5° and 15° with the longitudinal axis of the expander when in a relaxed state. The use of this embodiment is the same as that described with reference to the previous embodiment.

Figure 8:
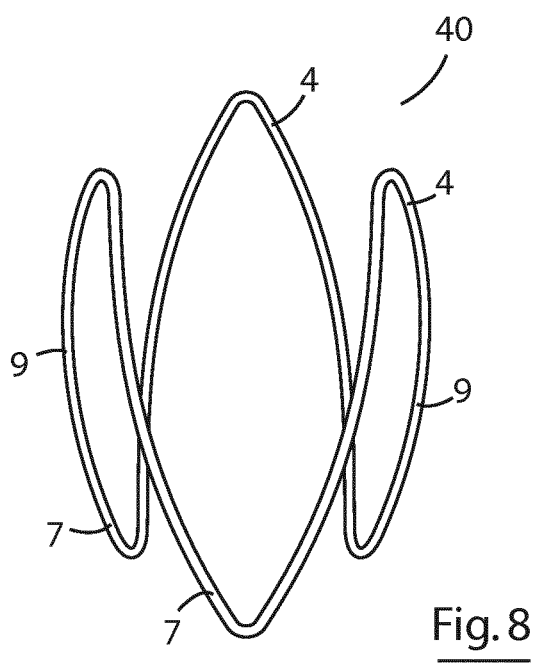
FIG. 8 is an elevational view of a three prong expander according to the invention comprising a barrel-shaped sinusoidal ring.

Referring to FIG. 8, there is illustrated an elevational view of an expander according to an alternative embodiment of the invention in which parts described with reference to the previous embodiments are assigned the same reference numerals. In this embodiment, the expander 40 has three distal prongs 4 and three proximal prongs 7, and the struts are curved outwardly along their length so that the expander has a substantially barrel shape along its length. The use of this embodiment is the same as that described with reference to the previous embodiment.

Figure 9:
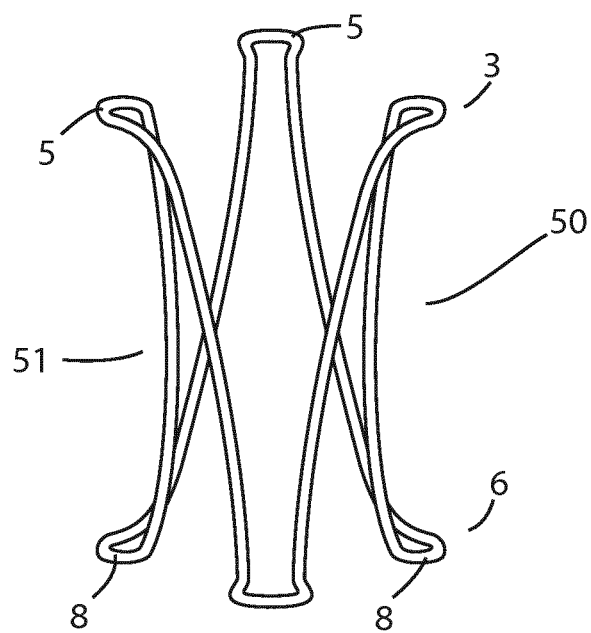
FIG. 9 is an elevational view of a three prong expander according to the invention comprising in which the apices of the prongs are flared outwardly.

Referring to FIG. 9, there is illustrated an elevational view of an expander according to an alternative embodiment of the invention in which parts described with reference to the previous embodiments are assigned the same reference numerals. In this embodiment, the expander 50 has three distal prongs 4 and three proximal prongs 7, and the struts are curved inwardly along their length so that the expander has a substantially waisted shape along its length, with a narrowed central portion 51 and slightly widened ends 3, 6. In addition, the apices 5, 8 at each end are flared outwardly. The use of this embodiment is the same as that described with reference to the previous embodiment.

Figure 10:
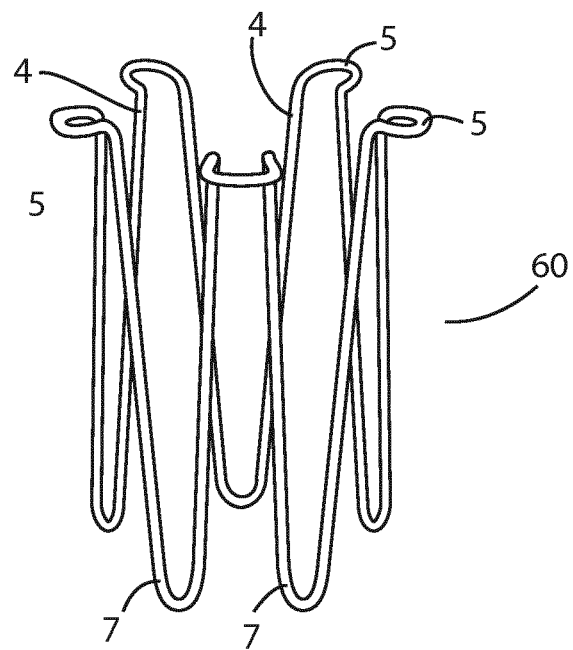
FIG. 10 is an elevational view of a three prong expander according to the invention in which the apices of the distal prongs are flared outwardly.

Referring to FIG. 10, there is illustrated an elevational view of an expander according to an alternative embodiment of the invention in which parts described with reference to the previous embodiments are assigned the same reference numerals. In this embodiment, the expander 60 has five distal prongs 4 and five proximal prongs 7, and the apices 5 at the distal end 3 are flared outwardly. The use of this embodiment is the same as that described with reference to the previous embodiment.

Figure 11:
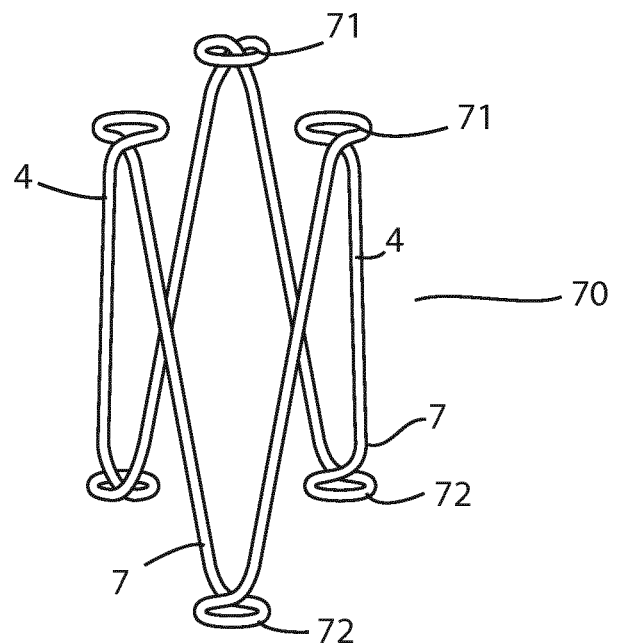
FIG. 11 is an elevational view of a three prong expander according to the invention in which the apices of the distal prongs comprise an inwardly flared loop and the apices of the proximal prongs comprise an outwardly flared loop.

Referring to FIG. 11, there is illustrated an elevational view of an expander according to an alternative embodiment of the invention in which parts described with reference to the previous embodiments are assigned the same reference numerals. In this embodiment, the expander 70 has three distal prongs 4 and three proximal prongs 7. The apices 5 at the distal end 3 are formed into loops 71 that project radially inwardly, and the apices 8 at the proximal end 6 are formed into loops 72 that project radially outwardly. The use of this embodiment is the same as that described with reference to the previous embodiment.

Figure 12:
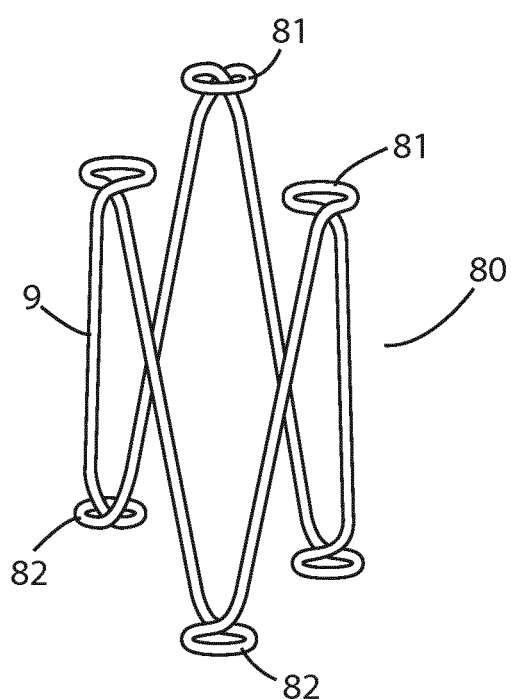
FIG. 12 is an elevational view of a three prong expander according to the invention similar to the expander of FIG. 12 and in which the distal prongs are offset in height and the proximal prongs are offset in height to allow the distal and proximal loops dovetail when the expander is in a contracted orientation.
Figure 13:
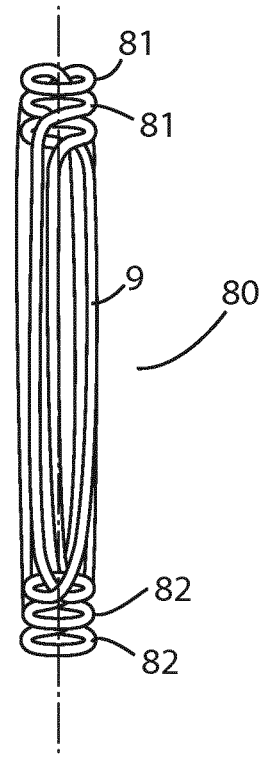
FIG. 13 is an elevational view of the three-prong expander of FIG. 12 shown in a contracted orientation.

Referring to FIGS. 12 and 13, there is illustrated an elevational view of an expander according to an alternative embodiment of the invention in which parts described with reference to the previous embodiments are assigned the same reference numerals. In this embodiment, the expander 80 has three distal prongs 4 and three proximal prongs 7. The apices 5 at the distal end 3 are formed into loops 81 that project radially inwardly, and the apices 8 at the proximal end 6 are formed into loops 82 that project radially outwardly. In addition, the longitudinal position of the distal and proximal prongs is offset enabling the loops 81 to dovetail when the expander is in a contracted orientation (shown in FIG. 13). The use of this embodiment is the same as that described with reference to the previous embodiment.

Figure 14:
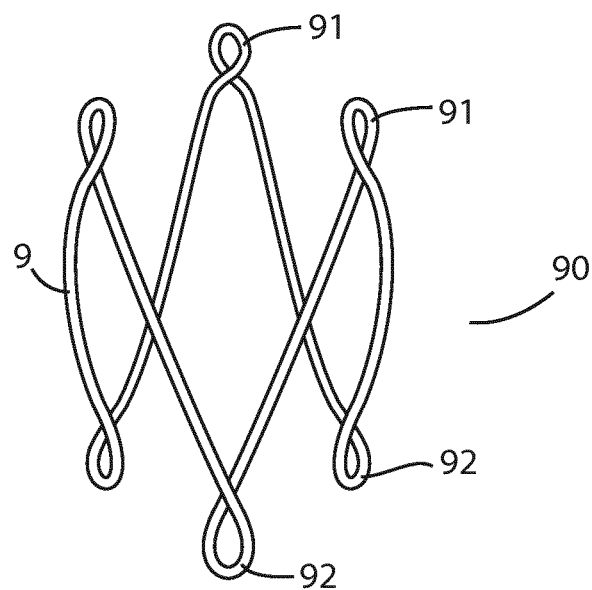
FIG. 14 is an elevational view of a three-prong expander of the invention having looped apices on the distal and proximal prongs.

Referring to FIG. 14, there is illustrated an elevational view of an expander according to an alternative embodiment of the invention in which parts described with reference to the previous embodiments are assigned the same reference numerals. In this embodiment, the expander 90 has three distal prongs 4 and three proximal prongs 7. The apices 5 at the distal end 3 are formed into loops 91 that project along a longitudinal axis of the expander, and the apices 8 at the proximal end 6 are formed into loops 92 that project along a longitudinal axis of the expander. In addition, the struts are curved outwardly. The use of this embodiment is the same as that described with reference to the previous embodiment.

Figure 15:
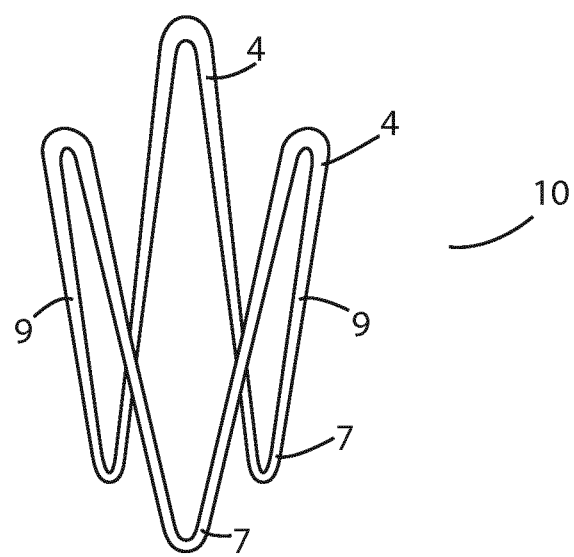
FIG. 15 is an elevational view of a three prong expander of the invention in which the struts of the distal prongs have a greater thickness that the struts of the proximal prongs.

Referring to FIG. 15, there is illustrated an expander according to an alternative embodiment of the invention in which parts described with reference to the previous embodiments are assigned the same reference numerals. In this embodiment, the expander 100 is formed of a nitinol wire that has a varying thick ness along its length, with the portions of the wire forming the distal prongs 4 being thicker that the portion of the wire that forms the proximal prongs 7. The use of this embodiment is the same as that described with reference to the previous embodiment.

Figure 16:
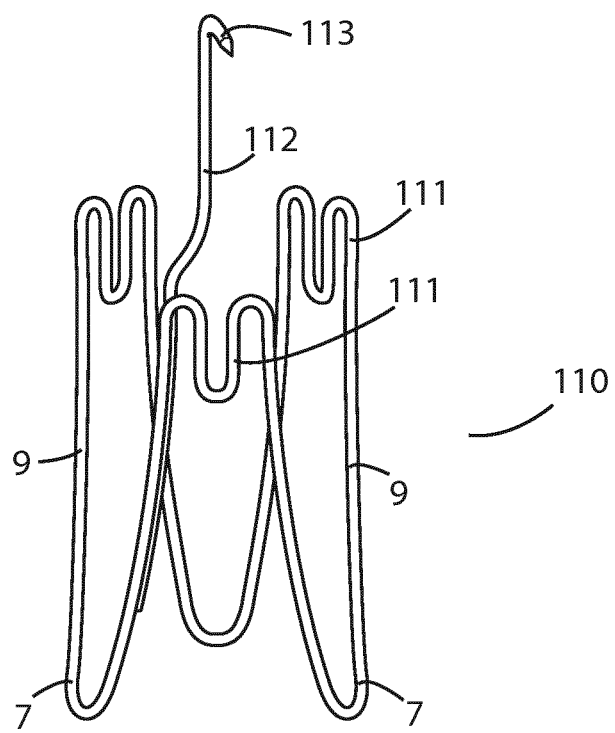
FIG. 16 is an elevational view of a three prong expander of the invention in which the apices of the distal prongs are formed into an M-formation, and in which an end of the wire extends beyond one of the apices to provide a fixation barb.

Referring to FIG. 16, there is illustrated an elevational view of an expander according to an alternative embodiment of the invention in which parts described with reference to the previous embodiments are assigned the same reference numerals. In this embodiment, the expander 110 has three distal prongs 4 and three proximal prongs 7. The apices 5 at the distal end 3 comprise M-shaped loops 111 that project along a longitudinal axis of the expander. In addition, the nitinol wire has an end 112 that extends beyond the distal end 3 of the expander and comprises a terminal barb 113 for fixing the expander in place (anchoring element). The use of this embodiment is the same as that described with reference to the previous embodiment.

Figure 17:
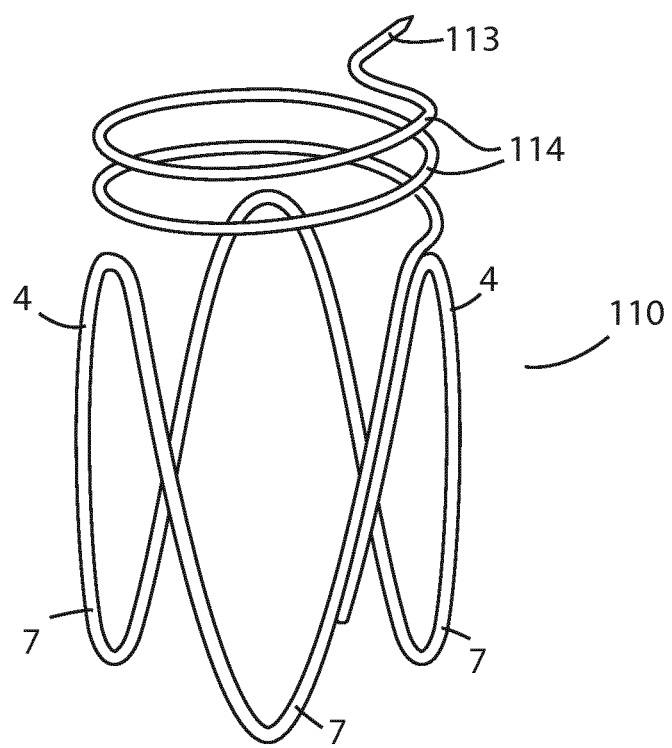
FIG. 17 is an elevational view of a three-prong expander of the invention in which an end of the wire extends beyond one of the apices to provide a coil having a barbed end.

Referring to FIG. 17, there is illustrated an elevational view of an expander according to an alternative embodiment of the invention in which parts described with reference to the previous embodiments are assigned the same reference numerals. This embodiment is similar to that of FIG. 16 with the exception that the end of the nitinol wire forms two helical loops 114 and terminates in a barb 113 for fixing the expander in place (anchoring element). The use of this embodiment is the same as that described with reference to the previous embodiment.

Figure 18:
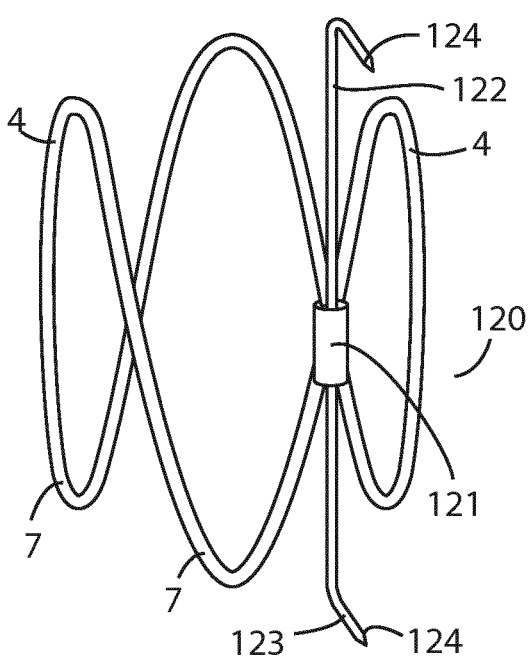
FIG. 18 is an elevational view of a three-prong expander of the invention in which each end of the wire extends longitudinally beyond the ends of the expander to provide distal and proximal barbs.

Referring to FIG. 18, there is illustrated an elevational view of an expander according to an alternative embodiment of the invention in which parts described with reference to the previous embodiments are assigned the same reference numerals. In this embodiment, the expander 120 has three distal prongs 4 and three proximal prongs 7 and is formed from a nitinol wire that overlaps at a joining point 121 and has ends 122 and 123 that extend longitudinally beyond the ends of the expander and comprise terminal barbs 124 for fixing the expander in place (anchoring element). The use of this embodiment is the same as that described with reference to the previous embodiment.

Figure 19:
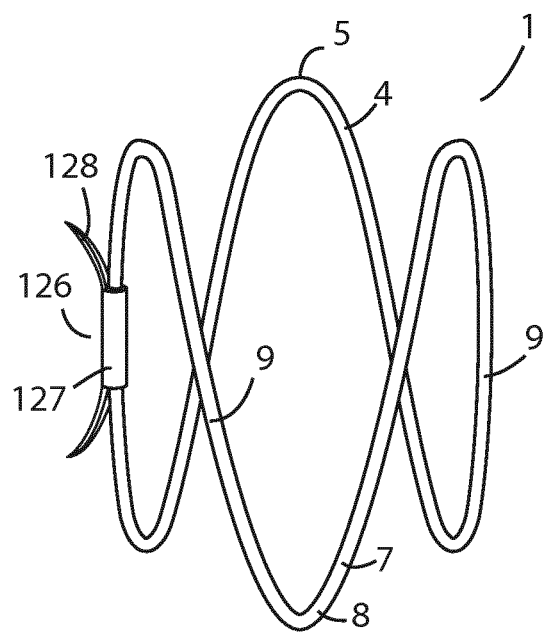
FIG. 19 is an elevational view of the three-prong expander of FIG. 1 having an anchoring element disposed on one of the longitudinal struts.

Referring to FIG. 19, there is illustrated an elevational view of an expander according to an alternative embodiment of the invention in which parts described with reference to the previous embodiments are assigned the same reference numerals. In this embodiment, the expander comprises an anchoring element 126 disposed on a longitudinal strut 9, the anchoring element comprising a strut-embracing sleeve 127 and upwardly projecting barbs 128.

Figure 20:
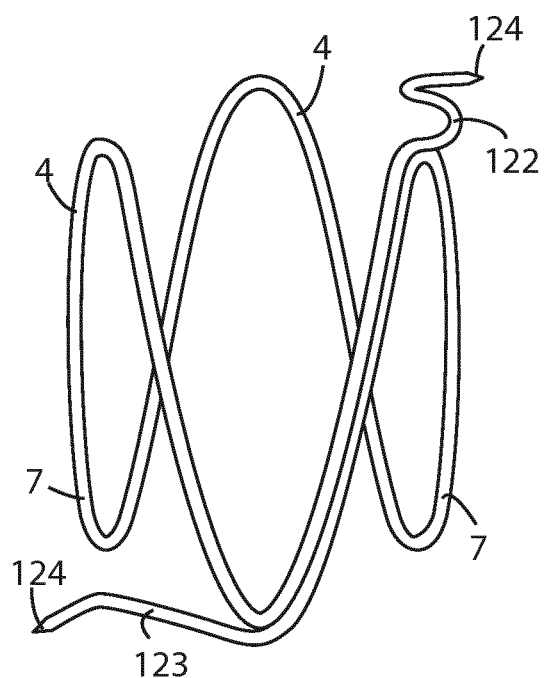
FIG. 20 is an elevational view of a three-prong expander of the invention in which each end of the wire extends longitudinally beyond the ends of the expander to provide distal and proximal barbs that extend circumferentially partially around each end of the expander.

Referring to FIG. 20, there is illustrated an elevational view of an expander according to an alternative embodiment of the invention in which parts described with reference to the previous embodiments are assigned the same reference numerals. This embodiment is similar to that of FIG. 18 with the exception that the ends 122 and 123 extend substantially circumferentially around each end of the expander and comprise terminal barbs 124 for fixing the expander in place. The use of this embodiment is the same as that described with reference to the previous embodiment.

Figure 21:
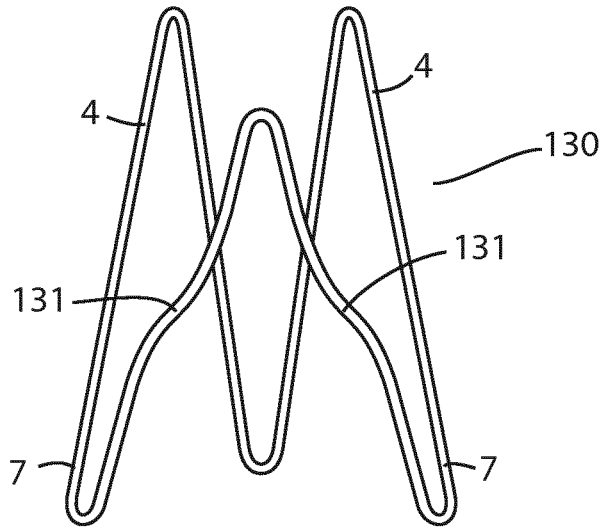
FIG. 21 is an elevational view of a three-prong expander of the invention in which four of the struts are substantially linear and four of the struts are non-linear.

Referring to FIG. 21, there is illustrated an elevational view of an expander according to an alternative embodiment of the invention in which parts described with reference to the previous embodiments are assigned the same reference numerals. In this embodiment, the expander 130 has three distal prongs 4 and three proximal prongs 7, and is longitudinally inwardly tapered towards the distal end 3 with the struts having an angle of between 5 and 15 degrees with the longitudinal axis of the expander when in a relaxed state. In addition, two adjacent struts 131 are cranked inwardly intermediate their ends providing a different angular spacing between the struts. The use of this embodiment is the same as that described with reference to the previous embodiment.

Figure 22:
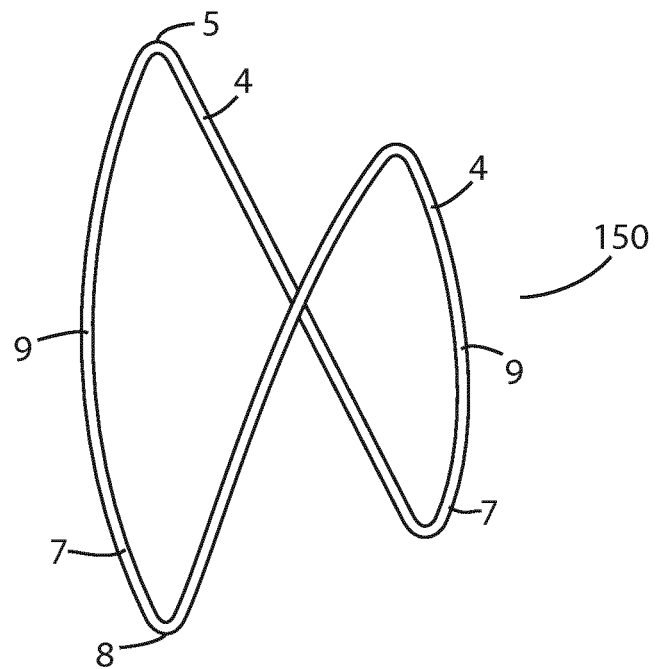
FIG. 22 is an elevational view of a two-prong expander of the invention shown in a relaxed expanded state.

Referring to FIG. 22, there is illustrated an elevational view of an expander according to an alternative embodiment of the invention in which parts described with reference to the previous embodiments are assigned the same reference numerals. In this embodiment, the expander 150 is substantially the same as the expander illustrated in FIG. 1 with the exception that the expander comprises two distal and proximal prongs 4, 7 instead of three. The operation of this embodiment is the same as the embodiment of FIG. 1.

Figure 23:
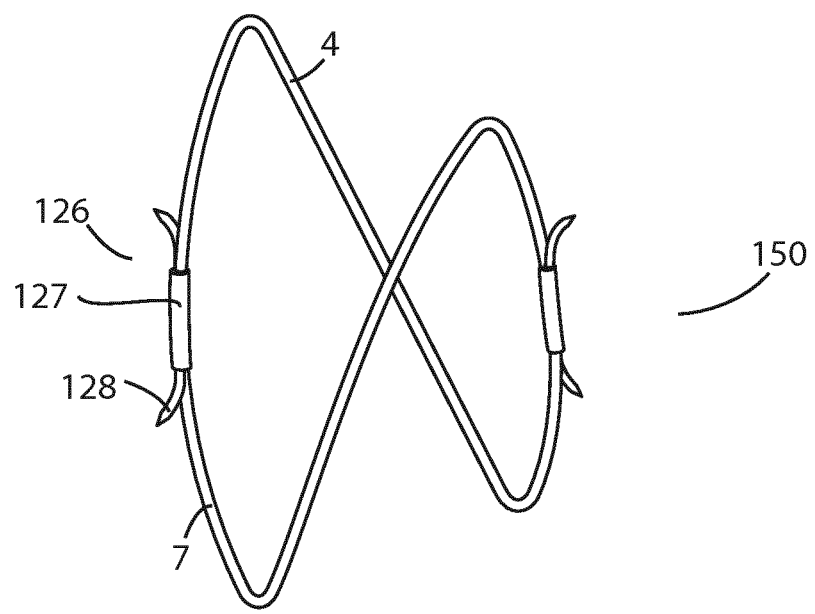
FIG. 23 is an elevational view of the two-prong expander of FIG. 22 in which two of the longitudinal prongs comprise anchoring elements.

Referring to FIG. 23, there is illustrated the expander of FIG. 22 having anchoring elements 126 disposed on longitudinal struts 9. Each anchoring element 126 comprises a sleeve 127 that embraces a strut 9 and a pair of barbs 128 that project away from the strut at right angles to each other.

Figure 24:
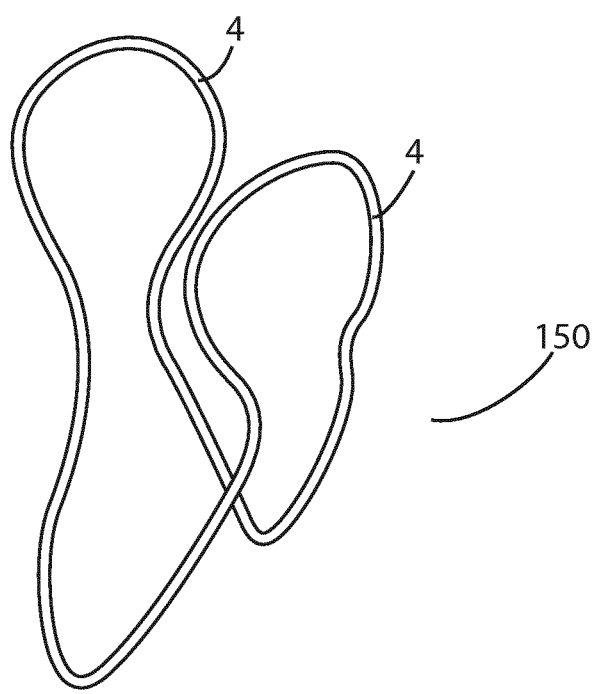
FIG. 24 is an elevational view of an alternative embodiment of two-prong expander of the invention shown in a relaxed expanded state.

Referring to FIG. 24, there is illustrated an elevational view of an expander according to an alternative embodiment of the invention in which parts described with reference to the previous embodiments are assigned the same reference numerals. In this embodiment, the expander 150 is substantially the same as the expander illustrated in FIG. 22 with the exception that the apices of the distal prongs 4 are rounded.

Figure 25:
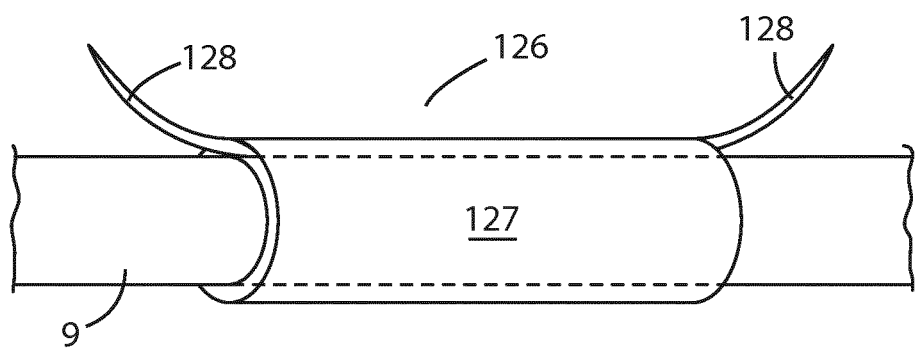
FIG. 25 is an elevational view of an anchoring element shown disposed on a strut of an expander of the invention.
Figure 26:
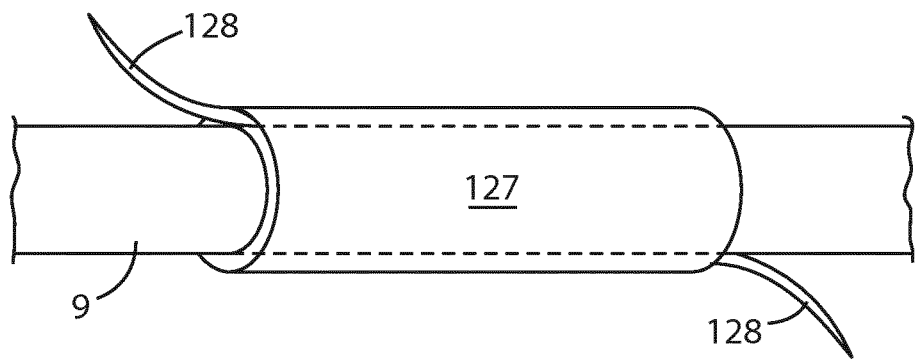
FIG. 26 is an elevational view of a further embodiment of anchoring element shown disposed on a strut of an expander of the invention.
Figure 27:
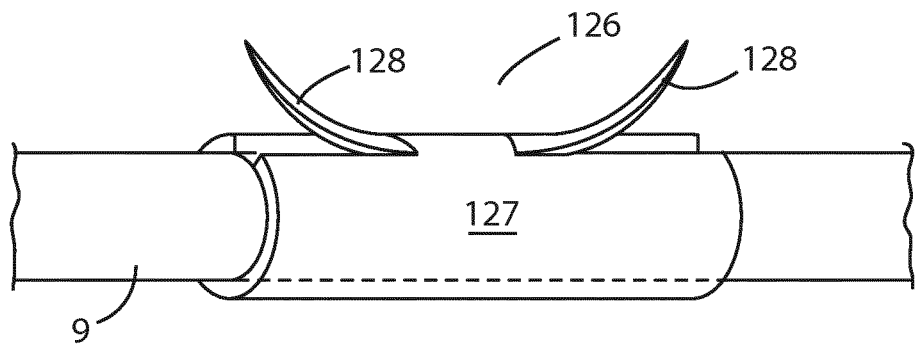
FIG. 27 is an elevational view of a further embodiment of anchoring element shown disposed on a strut of an expander of the invention.
Figure 28:
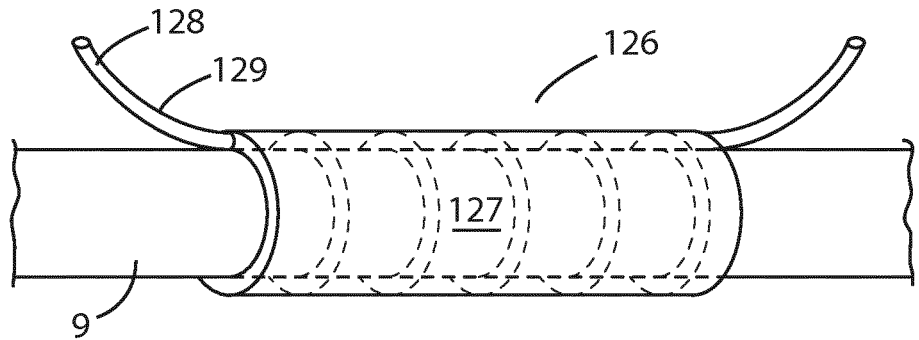
FIG. 28 is an elevational view of a further embodiment of anchoring element shown disposed on a strut of an expander of the invention.

Referring to FIGS. 25 to 28, there is illustrated a number of embodiments of anchoring elements 126, each comprising a sleeve 127 configured to embrace a strut 9 of an expander of the invention, and having barbs 128 that project away from the strut and when in-situ engage a wall of a body lumen. In the embodiment of FIG. 25, the barbs 128 are mounted at each end of a top of the sleeve 127 and project upwardly away from the strut at an angle of roughly 45 to the strut. In the embodiment of FIG. 26, one of the barbs 128 projects from a top of one end of the sleeve 127 and the other barb 128 projects from a bottom of an opposite end of the expander. In the embodiment of FIG. 27, the barbs 128 are cut-out from the top of the sleeve 127. In the embodiment of FIG. 28, a wire 129 is mounted to an inside of the sleeve 127 with each end of the wire 129 projecting proud of the sleeve forming the barbs 128.

Figure 29:
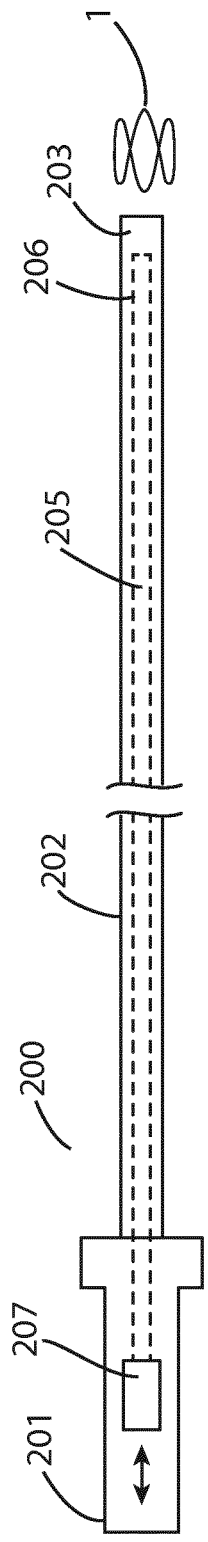
FIG. 29 is an elevational view of a delivery device for an expander of the invention prior to insertion of the expander.
Figure 30:
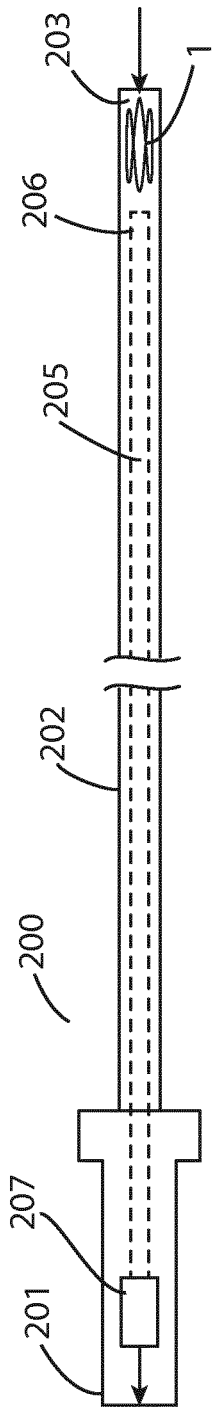
FIG. 30 is an elevational view of the delivery device of FIG. 20 showing the expander in-situ within the distal end of the device in a contracted orientation.
Figure 31:
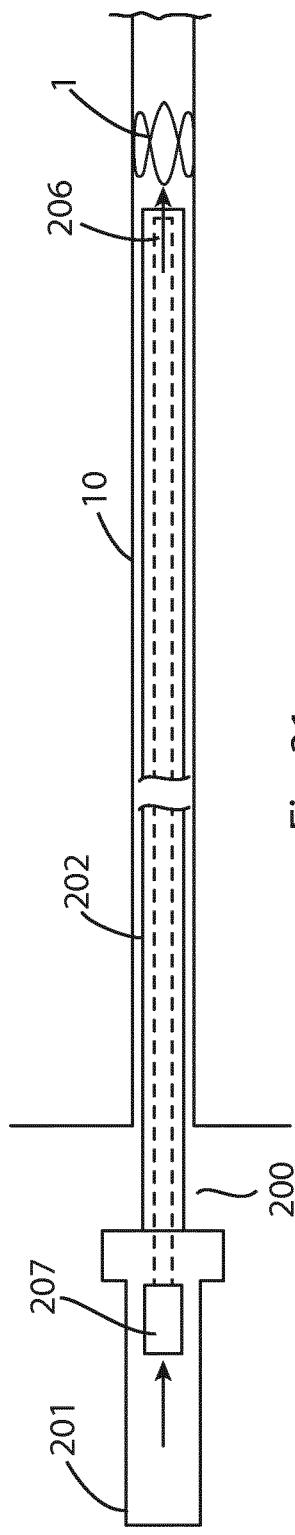
FIG. 31 is an elevational view of the delivery device of FIG. 20 showing the expander in-situ within the prostatic urethra after ejection from the distal end of the device.

Referring to FIGS. 29 to 31, there is illustrated a delivery device for delivering an expander of the invention to a target site within a body lumen, in this case delivery to the prostatic urethra. The device 200 comprises a handle 201, a delivery tube 202 having a having a hollow distal end 203 remote from the handle 201 configured to receive an expander of the invention in a contracted orientation, and an ejection element 205 operatively connected to the handle 201 and operable to eject a stent from the open end of the delivery tube. In more detail, the ejection means 205 comprises a shunt mechanism having a distal end 206 operatively connected to actuation means 207 on the handle and a proximal end disposed adjacent the distal end 203 of the tube 202. In use, the shunt mechanism is retracted and the expander 1 is compressed manually into a contracted shape and inserted into the hollow distal end of the delivery tube (FIG. 30). The delivery tube is then inserted into the urethra through the penis and advanced along the urethra until the distal end of the delivery tube is located within the prostatic urethra 10. The actuation means 207 on the handle is then actuated to extend the shunt mechanism and eject the expander 1 from the delivery tube into the prostatic urethra, where it expands to exert a radially outward pressure against the wall of the prostatic urethra (FIG. 31). The delivery tube is then retracted from the urethra.

Figure 32:
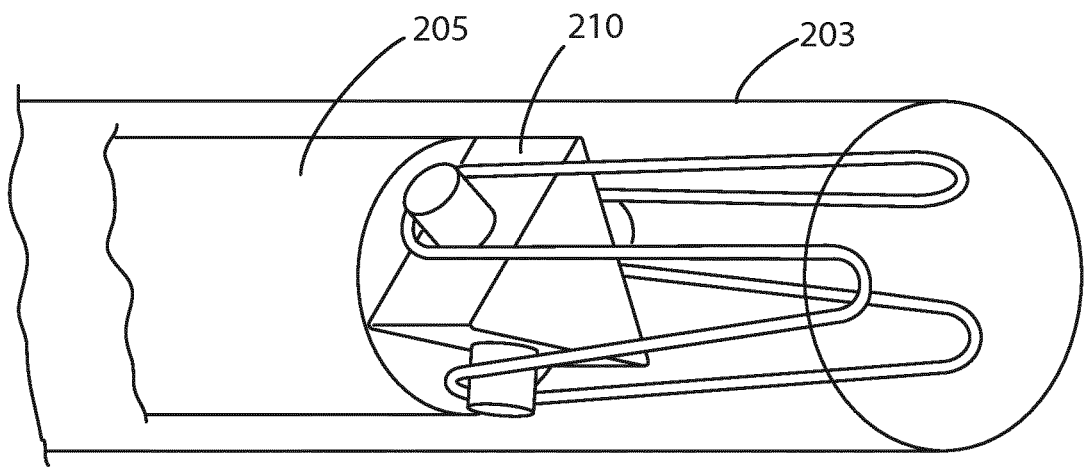
FIG. 32 is an elevational view of a distal end of an ejection element forming part of the delivery device of FIG. 29.

Referring to FIG. 32, there is provided a detailed elevational view of part of the delivery device 200 of FIG. 29. In this embodiment, the ejection element 205 includes a distal head 210 having a triangular cross-section and configured to fit within a lumen of the expander when it is mounted within the delivery tube 202. Each of the three faces of the head 210 include a projection 211 together forming a jig for positioning and engaging the expander within the delivery tube, each projection 211 being configured to engage an apex of a proximal prong of the expander. The manner of operation is the same as that described with reference to the embodiment of FIGS. 29 to 31, with the exception that the jig engages the expander enabling the ejection element both push and pull the expander along the delivery tube. This enables a surgeon partially eject the expander into the body lumen and then retract the expander if they feel that it is not in the correct position.

Figure 33:
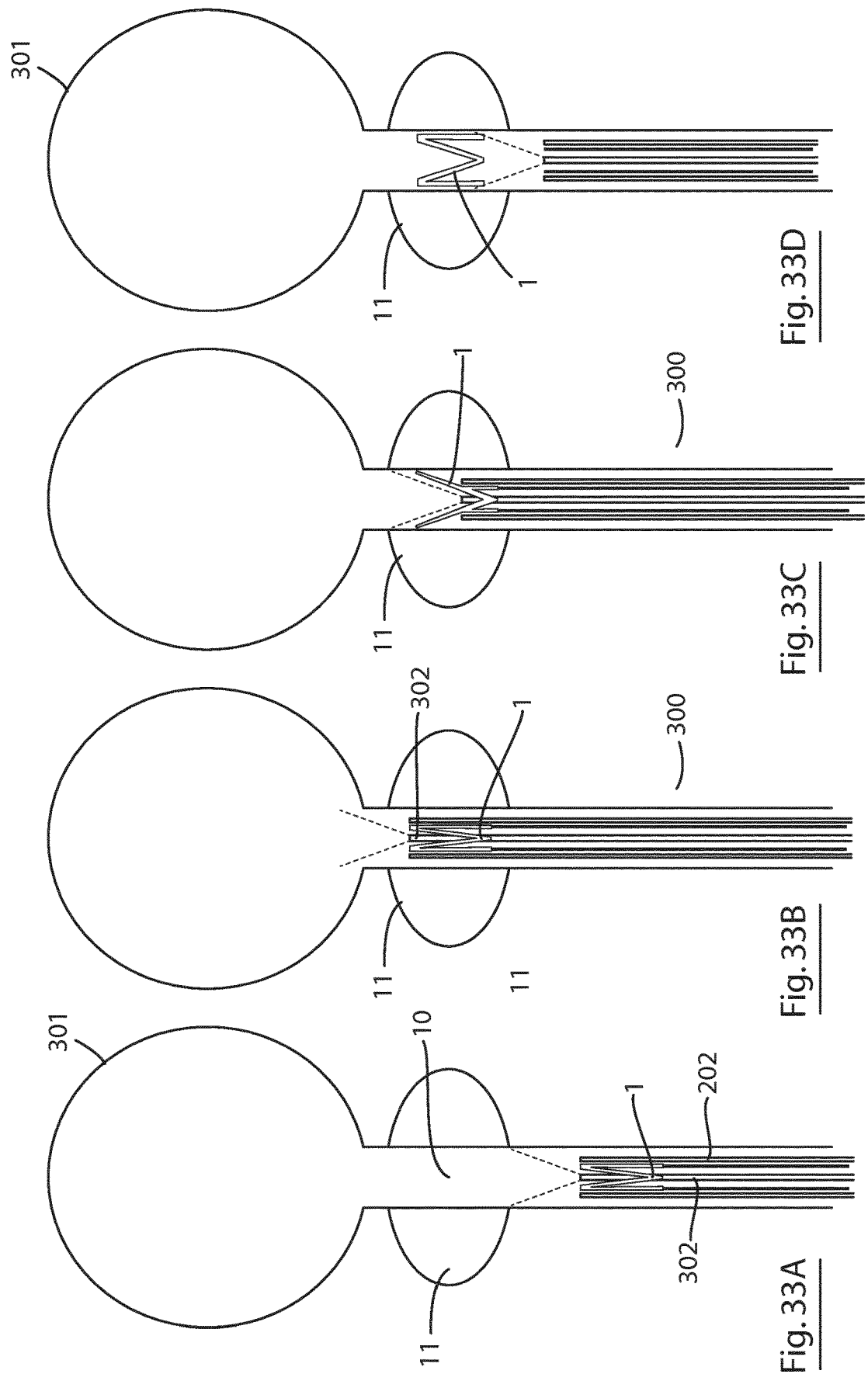
FIG. 33 (A to D) illustrate a delivery device of the invention incorporating a cystoscope disposed concentrically with a lumen of the delivery device in use delivering an expander of the invention in the prostatic urethra.
Figure 34:
FIG. 34 is a 3-D X-ray image showing an expander of the invention in-situ in the prostatic urethra of a canine.
Figure 35:
FIGS. 35 and 36 are photographs showing an expander of the invention deployed in the prostatic urethra of a canine. The verumontanum is the ridge at six o'clock in the photos.
Figure 36:
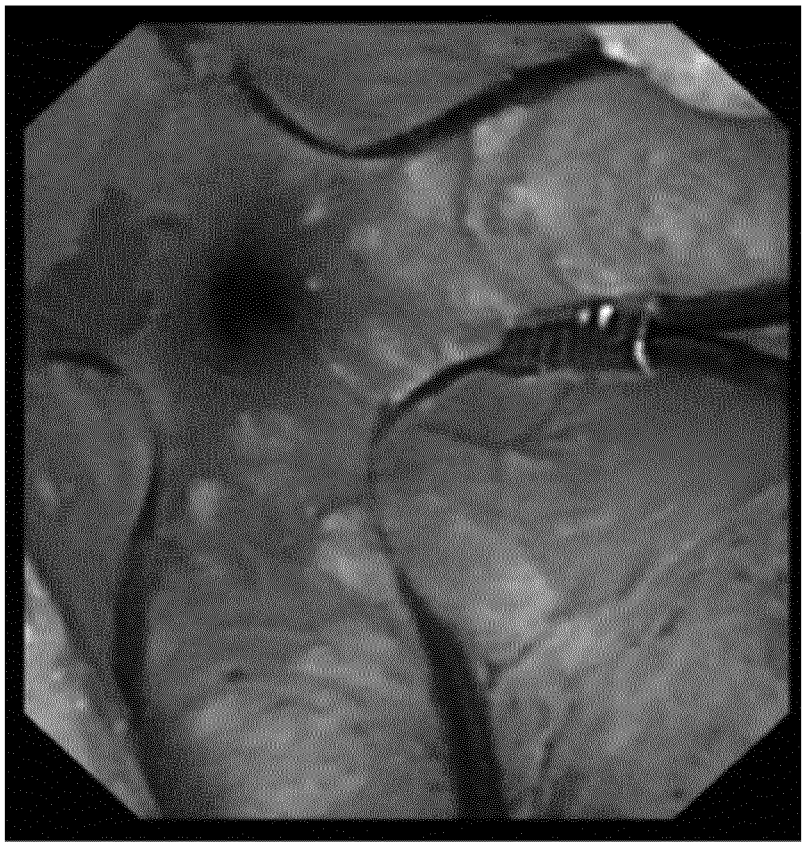

Referring to FIG. 33A to 33D, there is illustrated a delivery device of the invention 300 in use delivering an expander of the invention 1 into the prostatic urethra 10 which is surrounded by the prostate gland 11 and disposed distally of the bladder 301. The delivery device 300 includes a cystoscope 302 disposed concentrically within a lumen of the delivery device 300 and having a distal end substantially flush with a distal end of the delivery tube 202. As shown in FIG. 33A, the expander is mounted within the delivery tube 202 with the cystoscope 302 projecting through a lumen of the expander. The cystoscope comprises a light that illuminates the urethra distally of the end of the delivery device, thereby assisting a surgeon remotely image the urethra prior to deployment of the expander (FIG. 33B), and image the urethra and expander during deployment (FIG. 33C), and after deployment (FIG. 33D), of the expander.

Figure 37:
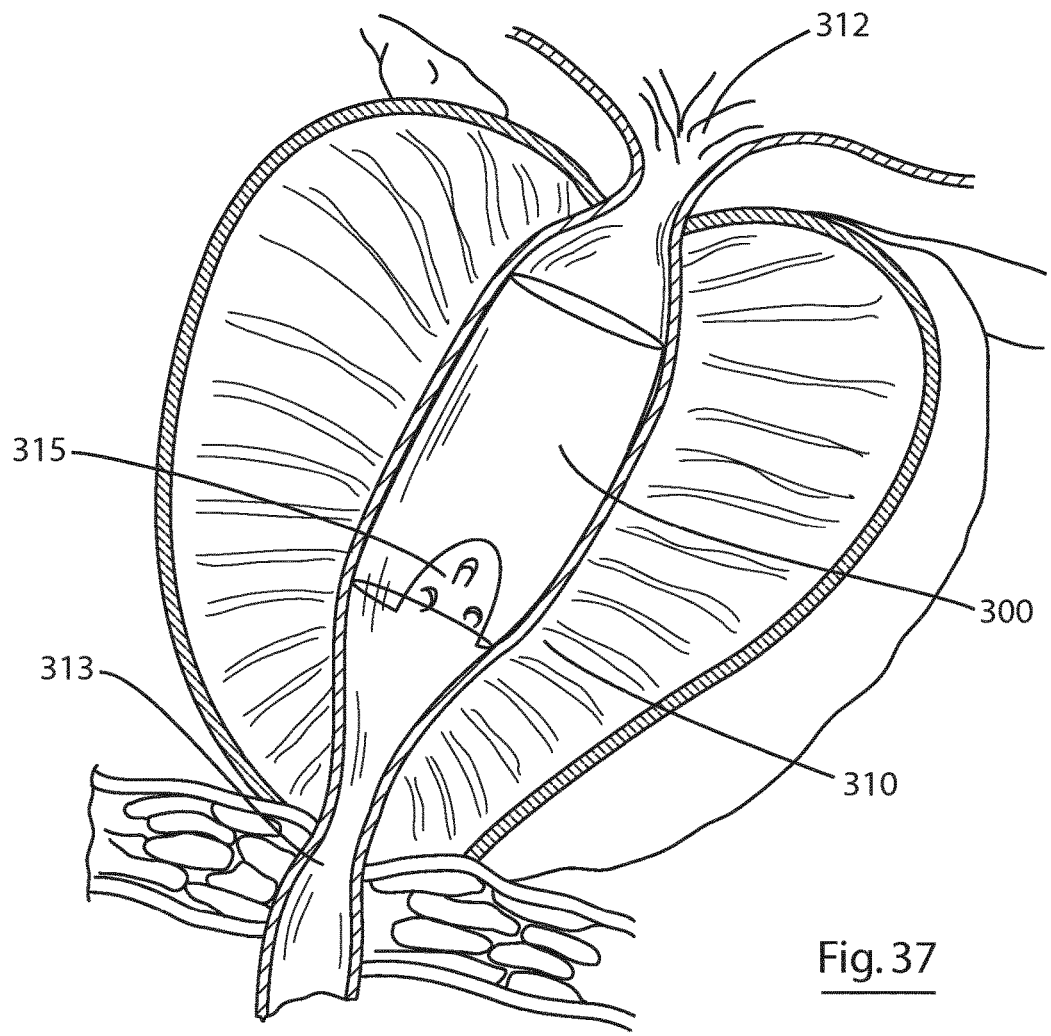
FIG. 37 illustrates a method of treating benign prostatic hyperplasia (BPH).

Referring to FIG. 37, a method of treating benign prostatic hyperplasia (BPH) is illustrated, in which an expander 300 is implanted into the prostatic urethra 310 between the bladder neck 312 and the external sphincter 313. The expander is capable of self-expansion between a radially contracted configuration (not shown, but employed during deployment) and a radially expanded configuration (shown) in which the expander dilates the prostatic urethra thereby relieving the patient of some of the symptoms of benign prostatic hyperplasia, in particular it widens the narrowed urethra, providing less resistance to urine during urination and allows the urine to pass through the diseased prostatic urethra (whereas before it would have encountered a narrowed, high pressure lumen). The expander is configured to fit in the prostatic urethra between the bladder neck 312 and external sphincter 313, so that it does not inhibit the function of either. As ejaculation requires the bladder neck to tonically contract and the external sphincter to spasm, the expander when properly positioned between the bladder neck and external sphincter allows for both of these functions, and thereby addresses one of the drawbacks of known implants for treating BPH, impaired ejaculation and sexual dysfunction. Moreover, as the function of the bladder neck is not compromised when the expander is in-situ, urine does not gather for long periods in the prostatic urethra thereby preventing encrustation of the expander. In addition, the expender is configured such that when deployed in-situ within the prostatic urethra and correctly positioned, blocking of the verumontanum 315 (and subsequent sexual dysfunction) is avoided. To this end, a proximal end of the expander 300 includes a suitably shaped cut-out 316 which prevents the sidewall of the expander 300 coming into contact with the verumontanum 315. In this embodiment, the expander 300 is not restricted to the undulating ring structure of previous embodiments, but may comprise any form of body such as for example the mesh-type bodies commonly employed in stents, or indeed any other type of body that is capable of adjustment between a radially contracted orientation suitable for delivery and a radially expanded orientation capable of dilating the prostatic urethra while allowing flow of urine.

Figure 38:
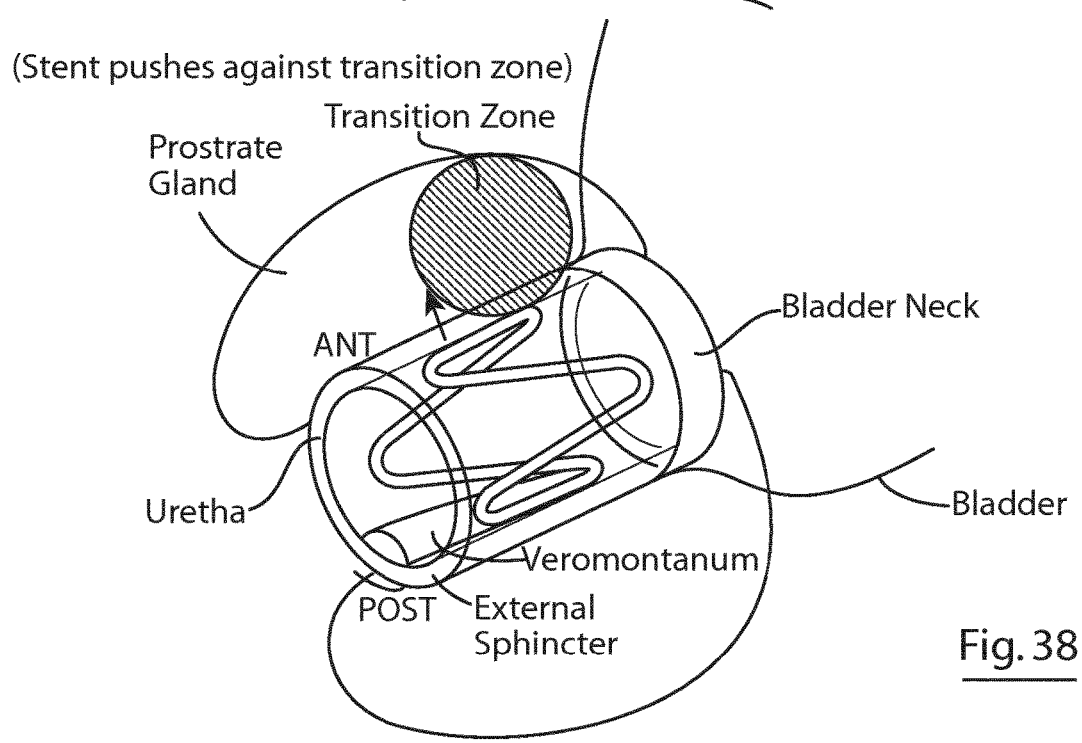
FIG. 38 illustrates an expander of the invention deployed in the prostatic urethra of a patient with BPH, between the bladder neck muscle and the external sphincter. This figure shows how the device accommodates the verumontanum between two prongs of the expander in the distal prostatic urethra, which the proximal end of the device is configured such that one of the prongs pushes the transition zone of the prostate gland away from the lumen of the prostatic urethra.

Referring to FIG. 38, an expander of the invention is shown deployed in the prostatic urethra of a patient with BPH, between the bladder neck muscle and the external sphincter. This figure shows how the device accommodates the verumontanum between two prongs of the expander in the distal prostatic urethra, while the proximal end of the device is configured such that one of the prongs pushes the transition zone of the prostate gland away from the lumen of the prostatic urethra.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. An implantable biocompatible expander suitable for treatment of benign prostatic hyperplasia (BPH), the expander comprising: a single elongated undulating ring having a proximal end comprising three proximal prongs, each proximal prong having a respective apex, and a distal end comprising three distal prongs, each distal prong having a respective distal apex, wherein the expander is resiliently deformable from a relaxed radially expanded configuration to a radially contracted configuration suitable for transluminal delivery through the urethra, respective longitudinal struts connecting each of the proximal apices to two of the distal apices and each of the distal apices to two of the proximal apices, whereby the expander is configured to span a substantial section of the prostatic urethra between the bladder neck and external sphincter and cause in-situ expansion of the substantial section of the prostatic urethra and whereby the expander has a triangular cross-sectional shape configured to match the triangular cross section of the prostatic urethra such that, in-situ, the proximal prongs are configured to sit in the most lateral triangular recesses of the prostatic urethra and the longitudinal struts are configured to engage the wall of the prostatic urethra.

2. An implantable biocompatible expander according to claim 1 in which the single elongated undulating ring is a single elongated sinusoidal ring.

3. An implantable biocompatible expander according to claim 1 having an anchoring element configured to anchor the expander in the prostatic urethra during use, in which at least a part of the anchoring element is biodegradable to facilitate release of the expander after a period of time.

4. An implantable biocompatible expander according to claim 3 in which the anchoring element comprises a strut-embracing collar and one or more projections extending proud of the collar.

5. An implantable biocompatible expander according to claim 1 in which the distal and proximal prongs are staggered angularly around the ring such that the distal and proximal prongs alternate with each other circumferentially.

6. An implantable biocompatible expander according to claim 1 wherein at least one of the distal and proximal apices comprises a loop or lip.

7. An implantable biocompatible expander according to claim 6 in which the loop or lip projects radially into the expander or radially out of the expander.

8. An implantable biocompatible expander according to claim 1 in which the elongated undulating ring is tapered inwardly at each end such that the expander is substantially barrel shaped.

9. An implantable biocompatible expander according to claim 1 in which the undulating ring comprises open areas between the longitudinal struts and the distal and proximal prongs, wherein a radially outwardly facing surface area of the prongs and struts is less than 5% of the total open areas.

10. An implantable biocompatible expander according to claim 1 in which the undulating ring is formed from wire having a cross-sectional diameter of 0.2 to 1.0 mm.

11. An implantable biocompatible expander according to claim 1 in which the undulating ring is formed from a single wire.

12. An implantable biocompatible expander according to claim 11 in which one end of the wire is configured to form an anchoring element.

13. An implantable biocompatible expander according to claim 1, in which the expander is configured to effect in-situ dilation of the prostatic urethra at the target location without blocking the verumontanum.

14. An implantable biocompatible expander according to claim 1, having a width at the proximal or distal end of from 6 mm to 30 mm when in the radially expanded configuration and a length between the proximal apices and the distal apices of from 10 mm to 45 mm.

15. An implantable biocompatible expander according to claim 1, wherein the expander has a length configured to span at least 50% of the length of the prostatic urethra between the bladder neck and the external sphincter.

16. An implantable biocompatible expander according to claim 1, wherein when in the contracted configuration, the expander has a cross-sectional area that is reduced by 70% or more compared to the cross-sectional area of the expander when in the relaxed configuration.

17. An implantable biocompatible expander according to claim 1, wherein a mutually-adjacent pair of longitudinal struts diverge proximally from one of the distal apices to create an open area between that pair of struts for, in-situ, accommodating the verumontanum between the struts of that pair.

18. An implantable biocompatible expander according to claim 1, wherein the longitudinal struts splay longitudinally away from the prongs.

19. An implantable biocompatible expander suitable for treatment of benign prostatic hyperplasia (BPH), wherein:
the expander comprises a single elongated undulating ring having a proximal end comprising three proximal prongs, each proximal prong having a respective proximal apex, and a distal end comprising three distal prongs, each distal prong having a respective distal apex;
the expander is resiliently deformable from a relaxed radially expanded configuration to a radially contracted configuration suitable for transluminal delivery through the urethra;
respective longitudinal struts connect each of the proximal apices to two of the distal apices and each of the distal apices to two of the proximal apices, whereby the expander is configured to span a substantial section of the prostatic urethra between the bladder neck and the external sphincter and cause in-situ expansion of the substantial section of the prostatic urethra; and
a mutually-adjacent pair of the longitudinal struts diverge proximally from one of the distal apices to create an open area between that pair of struts for, in-situ, accommodating the verumontanum between the struts of that pair.

20. The biocompatible implantable expander of claim 19, wherein the expander has a triangular cross sectional shape configured to match the triangular cross section of the prostatic urethra such that, in-situ, the proximal prongs are configured to sit in the most lateral triangular recesses of the prostatic urethra.

* * * * *